United States Patent
Choncholas

(10) Patent No.: US 8,469,027 B2
(45) Date of Patent: Jun. 25, 2013

(54) APPARATUS AND METHOD FOR IDENTIFYING FRC AND PEEP CHARACTERISTICS

(75) Inventor: Gary J. Choncholas, Madison, WI (US)

(73) Assignee: General Electric Company, Schenectady, NY (US)

(*) Notice: Subject to any disclaimer, the term of this patent is extended or adjusted under 35 U.S.C. 154(b) by 116 days.

(21) Appl. No.: 13/240,383

(22) Filed: Sep. 22, 2011

(65) Prior Publication Data
US 2012/0055476 A1 Mar. 8, 2012

Related U.S. Application Data

(60) Division of application No. 11/438,244, filed on May 22, 2006, now abandoned, which is a continuation-in-part of application No. 11/358,573, filed on Feb. 21, 2006, now abandoned.

(60) Provisional application No. 60/719,329, filed on Sep. 21, 2005.

(51) Int. Cl.
A61M 16/00 (2006.01)

(52) U.S. Cl.
USPC ............ 128/204.23; 128/200.24; 128/204.18; 128/204.21

(58) Field of Classification Search
USPC ............ 128/200.24, 203.12, 203.15, 203.25, 128/204.18, 204.21, 204.22, 204.23, 204.26–204.28, 205.11; 600/529, 532
See application file for complete search history.

(56) References Cited

U.S. PATENT DOCUMENTS

| 4,307,730 A | 12/1981 | Korn |
| 4,333,476 A | 6/1982 | Downing, Jr. |
| 5,088,332 A | 2/1992 | Merilianen et al. |
| 5,513,647 A | 5/1996 | Castile |
| 5,540,233 A | 7/1996 | Larsson et al. |

(Continued)

FOREIGN PATENT DOCUMENTS

| EP | 640357 | 3/1995 |
| EP | 653183 | 5/1995 |

(Continued)

OTHER PUBLICATIONS

Burchardi et al., "Determination of Lung Volume in the ICU", Yearbook of Intesive Care and Emergency Medicine, 1998, 353-360.

(Continued)

Primary Examiner — Annette Dixon
(74) Attorney, Agent, or Firm — Andrus, Sceales, Starke & Sawall, LLP

(57) ABSTRACT

A patient ventilator for assisting a clinician in determining a suitable PEEP for the patient. The amount of the lung volume recruited/de-recruited at various levels of PEEP may be determined for use in selecting a desired PEEP. To this end, the functional residual capacity of the lungs is determined for a first PEEP level. The PEEP is then altered to a second level and a spirometry dynostatic curve of lung volume and pressure data is obtained. The lung volume on the dynostatic curve at a lung pressure corresponding to the first PEEP value is obtained. The difference between the functional residual capacity of the lungs at the first PEEP level and that determined from the dynostatic curve represents the lung volume recruited/de-recruited when changing between said first and second PEEPs.

20 Claims, 12 Drawing Sheets

U.S. PATENT DOCUMENTS

| | | | |
|---|---|---|---|
| 5,575,283 | A | 11/1996 | Sjoestrand |
| 5,615,669 | A | 4/1997 | Olsson et al. |
| 5,660,170 | A | 8/1997 | Rajan et al. |
| 5,915,381 | A | 6/1999 | Nord |
| 5,937,854 | A | 8/1999 | Stenzler |
| 5,957,128 | A | 9/1999 | Hecker et al. |
| 6,135,105 | A | 10/2000 | Lampotang et al. |
| 6,139,506 | A | 10/2000 | Heinonen |
| 6,158,432 | A | 12/2000 | Biondi et al. |
| 6,273,855 | B1 | 8/2001 | Schmid et al. |
| 6,306,099 | B1 | 10/2001 | Morris |
| 6,315,739 | B1 | 11/2001 | Merilainen et al. |
| 6,544,191 | B2 | 4/2003 | Koch et al. |
| 6,709,405 | B2 | 3/2004 | Jonson |
| 6,840,241 | B2 | 1/2005 | Strom |
| 7,465,275 | B2 | 12/2008 | Stenqvist |
| 7,530,353 | B2 * | 5/2009 | Choncholas et al. .... 128/204.18 |
| 7,681,574 | B2 | 3/2010 | Heinonen |
| 2004/0003813 | A1 | 1/2004 | Banner et al. |

FOREIGN PATENT DOCUMENTS

| | | |
|---|---|---|
| EP | 671180 | 9/1995 |
| EP | 791327 | 8/1997 |
| WO | 02096289 | 12/2002 |

OTHER PUBLICATIONS

East et al., "Automated sulfur hexafluoride washout functional residual capacity measurement system for any mode of mechanical ventilation as well as spontaneous respiration", Critical Care Medicine, 1990, 18(1):8491.

Fretschner et al., "A Simple Method to Estimate Functional Residual Capacity in Mechanically Ventilated Patients", Intensive Care Medicine, 1993, 19:372-376.

Hedensteirna, "The recording of FRC—Is it of importance and can it be made simple?", Intensive Care Medicine, 1993, 19:365-366.

Olegard et al., "Estimation of functional residual capacity at the bedside using standard monitoring equipment: A modified nitogen washout/washin technique requiring a small change of the inspired oxygen fraction", Aneseth Analg., 2005, 101:206-212.

Sondergaard, "The dynostatic algorithm in adult paediatric respiratory monitoring", Thesis, University Hospital, Gothenburg University, Sweden, 2002.

Stenqvist, "Practical assessment of respiratory mechanics", British Journal of Anaesthesia, 2003, 91(1):92-105.

"The Nitrogen-Washout Method for Measuring FRC", The Biomedical Engineering Handbook, CRC Press, 1995, 1237-1238.

"The lungs INview: SpiroDynamics and FRC INview take lung measurement capability to a new level", Window Magazine, Sep. 2, 2005, 3:22-23.

Partial European Search Report dated Feb. 27, 2009.

Partial European Search Report dated Sep. 18, 2009.

* cited by examiner

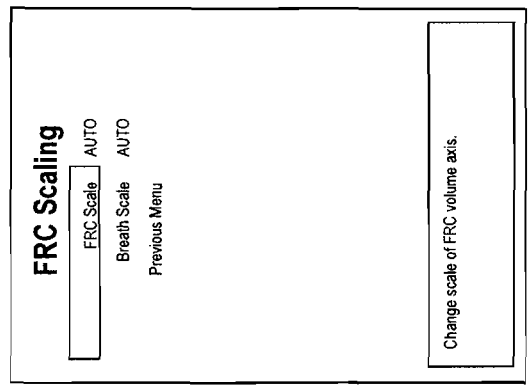
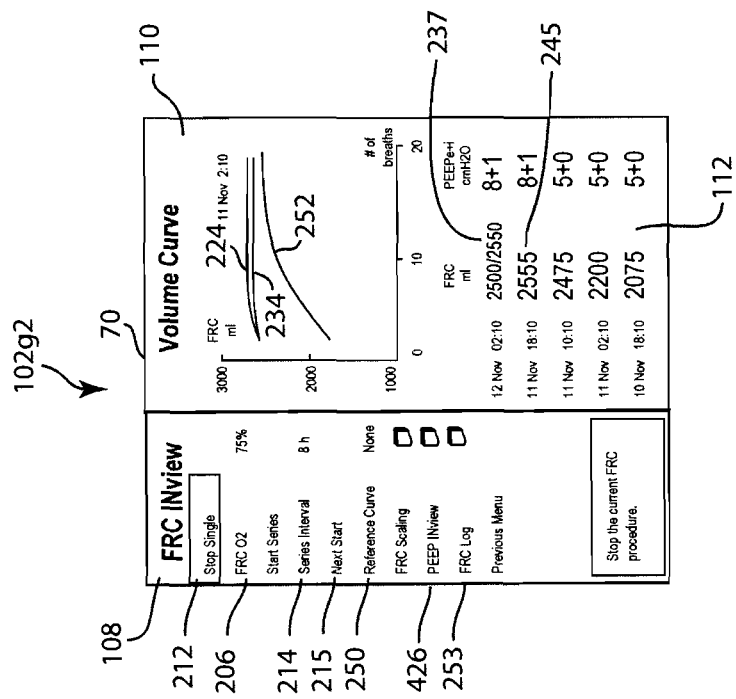
FIG. 6
FIG. 5

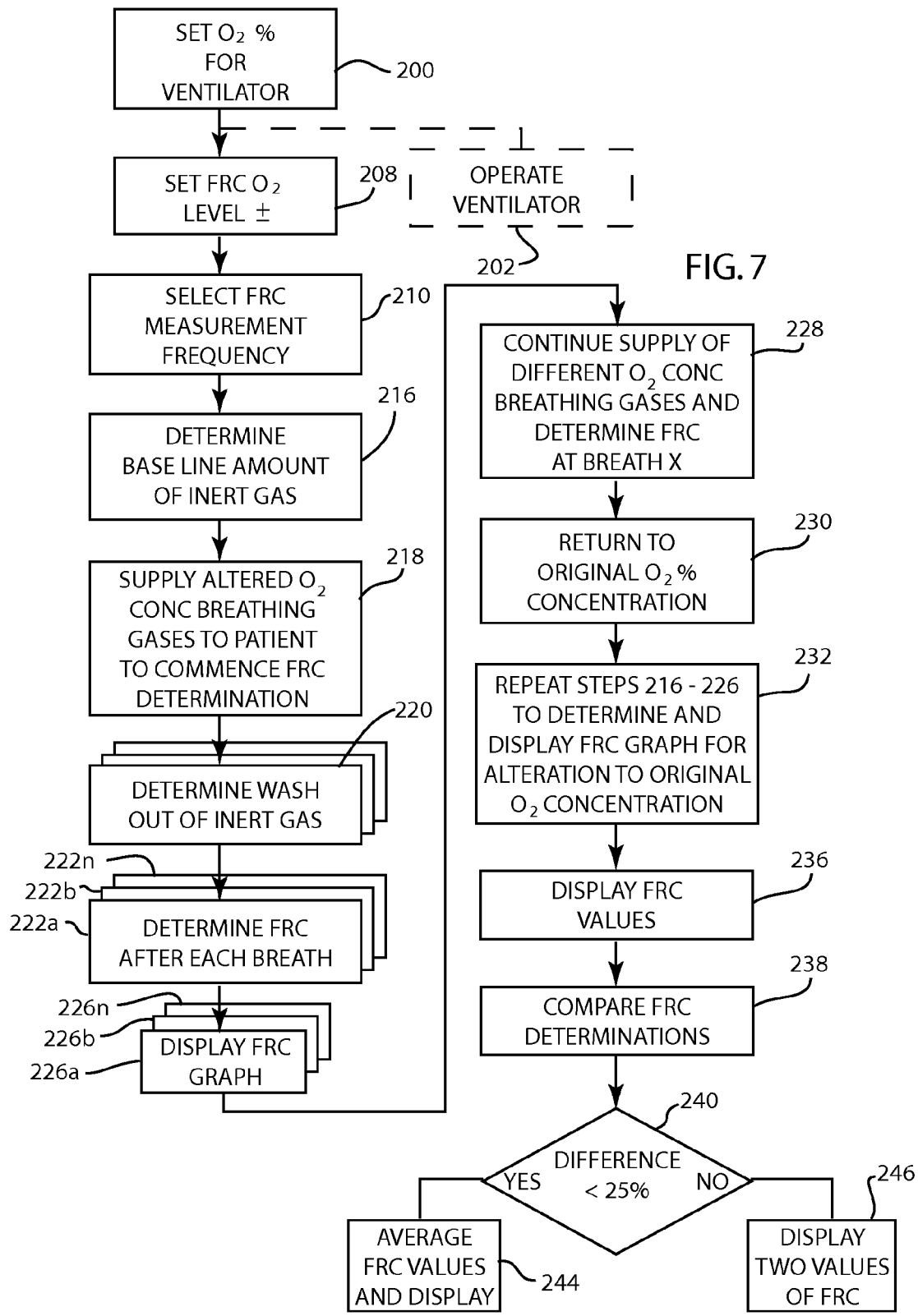

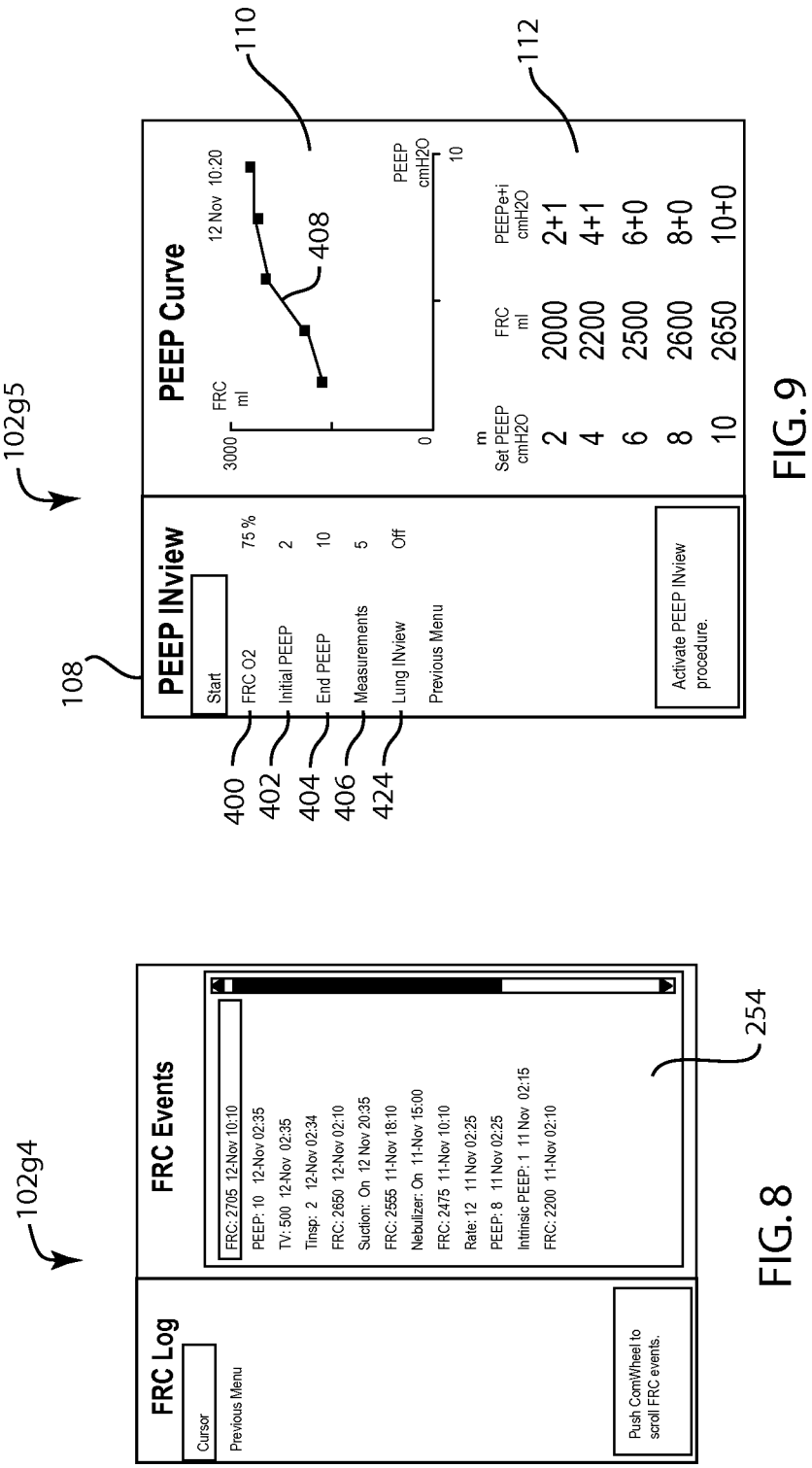

100
APPARATUS AND METHOD FOR IDENTIFYING FRC AND PEEP CHARACTERISTICS

CROSS REFERENCE TO RELATED APPLICATION

The present application is a divisional application of U.S. patent application Ser. No. 11/438,244, filed on May 22, 2006, published as US20070062533 on Mar. 22, 2007, which application claims the priority of U.S. Provisional Application No. 60/719,329, filed Sep. 21, 2005, and comprises a continuation-in-part of U.S. patent application Ser. No. 11/358,573, filed Feb. 21, 2006, which application also claims priority of U.S. Provisional Application No. 60/719,329, the contents of both U.S. Provisional Application No. 60/719,329 and U.S. patent application Ser. No. 11/358,573 are incorporated herein by reference in their entireties.

BACKGROUND AND SUMMARY

The present invention relates to an apparatus and method for determining and displaying functional residual capacity data and other pulmonary parameters, such as positive end expiratory pressure (PEEP) data, for patients breathing with the aid of a mechanical ventilator, such as a critical care ventilator. The invention also determines and displays relationships between these and other parameters.

Functional residual capacity (FRC) is the gas volume remaining in the lungs after unforced expiration or exhalation. Several methods are currently used to measure functional residual capacity. In the body plethysmography technique, the patient is placed in a gas tight body box. The patient's airway is sealingly connected to a breathing gas conduit connected to the exterior of the body box. By measuring lung pressures and pressures in the box, at various respiratory states and breathing gas valve flow control conditions, the functional residual capacity of the patient can be determined.

Another technique for measuring functional residual capacity is the helium dilution technique. This is a closed circuit method in which the patient inhales from a source of helium of known concentration and volume. When the concentration of helium in the source and in the lungs has reached equilibrium, the resulting helium concentration can be used to determine the functional residual capacity of the patient's lungs.

A further technique for determining functional residual capacity is the inert gas wash-out technique. This technique is based on a determination of the amount of gas exhaled from the patient's lungs and corresponding changes in gas concentrations in the exhaled gas. The gas used for the measurement is inert in the sense that it is not consumed by metabolic activity during respiration. While a number of gases may be used for such a measurement of functional residual capacity, it is convenient to use nitrogen for this purpose.

In a straightforward example in which the patient is initially breathing air, the lung volume forming the functional residual capacity of the lung will contain nitrogen in the same percentage as air, i.e. approximately 80%, the remaining 20% of air being oxygen. In a wash-out measurement, the subject commences breathing gases in which oxygen is at a different concentration than 20%. For example, the patient commences breathing pure oxygen. With each breath, nitrogen in the lungs is replaced by oxygen, or, stated conversely, the nitrogen is "washed out" of the lungs by the oxygen. While the breathing of pure oxygen could continue until all nitrogen is washed out of the lungs, in most cases, the breathing of oxygen continues until the nitrogen concentration in the exhaled breathing gases falls below a given concentration. By determining the volume of inert gas washed out of the lungs, and knowing the initial concentration of the inert gas in the lungs, the functional residual capacity of the lungs may be determined from these quantities.

Methods for determining functional residual capacity in this manner are well known and are described in such literature as The Biomedical Engineering Handbook, CRC Press, 1995, ISBN 0-8493-8346-3, pp. 1236-1239, Critical Care Medicine, Vol. 18, No. 1, 1990, pp. 8491, and the Yearbook of Intensive Care and Emergency Medicine, Springier, 1998, ISBN 3-540-63798-2, pp. 353-360. By analogy to the above described wash out measurement technique, it is also possible to use a wash in of inert gas for measurement of functional residual capacity. Such a method and apparatus is described in European Patent Publication EP 791,327.

The foregoing methods are used with spontaneously breathing patients and are typically carried out in a respiratory mechanics laboratory. But in many cases, patients that could benefit from a determination of functional residual capacity are so seriously ill as to not be breathing spontaneously but by means of a mechanical ventilator, such as a critical care ventilator. This circumstance has heretofore proven to be a significant impediment in obtaining functional residual capacity information from such patients. Additionally, the patient's illness may also make it impossible or inadvisable to move the patient to a laboratory or into and out of a body box for the determination of functional residual capacity.

It would therefore be highly advantageous to have an apparatus and method by which the functional residual capacity of mechanically ventilated patients could be determined. It would be further advantageous to associate the apparatus for carrying out the determination of functional residual capacity with the ventilator to reduce the amount of equipment surrounding the patient and to facilitate set up and operation of the equipment by an attending clinician. Such apparatus would also enable the determination of functional residual capacity to be carried out at the bedside of the patient, thus avoiding the need to move the patient.

A single determination of functional residual capacity provides important information regarding the pulmonary state of the patient. However, it is often highly desirable from a diagnostic or therapeutic standpoint to have available trends or changes in the functional residual capacity of a patient over time.

It would also be helpful to be able to relate functional residual capacity to other pulmonary conditions existing in the lungs or established by the ventilator and to changes in these conditions. For example, it is known that the pressure established by the ventilator in the lungs at the end of expiration, the positive end expiratory pressure or PEEP, affects the functional residual capacity of the lungs.

Typically, an increase in PEEP increases functional residual capacity. There are two components to the increased functional residual capacity as PEEP is increased. One component is due to stretching of the lung by the increased pressure. A second component, particularly in diseased lungs, occurs from the effect of PEEP during breathing by the patient. As a patient expires, the pressure in the lungs drops until it approaches airway pressure. As the pressure within the lungs drops, the alveoli or air sacs in the lungs deflate. If alveolar sacs collapse completely, more pressure is required upon inspiration to overcome the alveolar resistance and re-inflate the alveolar sacs. If this resistance cannot be overcome, the volume of such sacs are not included in the functional residual capacity of the patient's lungs.

By applying PEEP, in the patient's airway, the additional pressure in the patient's lungs keeps more of these alveolar sacs from completely collapsing upon expiration and, as such, allows them to participate in ventilation. This increases the functional residual capacity of the patient's lungs and the increase is often described as "recruited volume." Volume reductions are termed "de-recruitments."

However, setting the PEEP too high can cause excessive lung distension. There may also be compression of the pulmonary bed of the lung, loading the right side of the heart and reducing the blood volume available for gas exchange. Either of these circumstances present the possibility of adverse consequences to the patient.

It would, therefore, be desirable to provide an apparatus and method by which a clinician could quickly, easily, and definitely determine an optimal PEEP for a given patient at a given point in the therapeutic regimen for the patient. An optimal PEEP is one that keeps the lung open but avoids overpressurization of the lung. It is often termed the "open lung PEEP."

Still further, action such as performing a suction routine, administering a nebulized medication, or changing the ventilation parameters of the ventilator can also influence functional residual capacity and it would be helpful to be able to easily determine the effect of such actions on functional residual capacity.

An apparatus and method that would possess the foregoing characteristics and that would easily and cogently make such information available would be highly beneficial in conveniently obtaining a full understanding of the pulmonary condition of the patient and how the patient is reacting to the mechanical ventilation and to any associated therapeutic measures. The clinician could then carry out appropriate action beneficial to the patient in a timely and informed manner.

BRIEF DESCRIPTION OF THE PRESENT INVENTION

An embodiment of the present invention comprises an apparatus and method that achieves the highly advantageous features noted above. Thus, with the present invention the functional residual capacity of a mechanically ventilated patient may be determined at the bedside of the patient without the need to move the patient to a laboratory. By associating the apparatus with the ventilator, only a single device need be employed to both ventilate the patient and determine functional residual capacity.

The determined functional residual capacity may be advantageously displayed in conjunction with earlier determinations and in conjunction with other pulmonary conditions, such as PEEP. Changes, or trends, in functional residual capacity over time may thus be discerned, along with changes in the other pulmonary conditions.

The foregoing provides an attending clinician with significant information for assessing the state of, and trends in, the functional residual capacity of the patient, as well as the relationship between the patient's residual capacity and the other factors, so that the clinician can fully discern the functional residual capacity condition of the patient.

With respect to assisting the clinician in adequately determining an optimal PEEP for the patient, as noted above, the apparatus and method of the present invention determines and displays related PEEP and functional residual capacity values. This enables the clinician to note, for example, the point at which increases in PEEP produce little, if any, further increases in functional residual capacity.

The apparatus and method of the present invention also determines and displays a showing of the amount of lung volume recruited or de-recruited as the PEEP is changed. This allows the clinician to distinguish between changes in functional residual capacity due to lung stretching or contracting and those arising from recruitment or de-recruitment.

Further features of the apparatus and method of the present invention will be apparent from the following detailed description, taken in conjunction with the associated drawing.

BRIEF DESCRIPTION OF THE DRAWINGS

FIG. 5 shows a display screen for displaying functional residual capacity data and related data.

FIG. 6 shows a display for use in scaling the display shown in FIG. 5.

FIG. 7 is a flow chart showing the steps for carrying out a measurement of functional residual capacity.

FIG. 8 shows a display displaying a log of events and actions that may impact the determination of functional residual capacity.

FIG. 9 shows a display showing the effect of changes in PEEP on functional residual capacity.

DETAILED DESCRIPTION

The Mechanical Ventilator and Airway Gas Module

Figure 1:
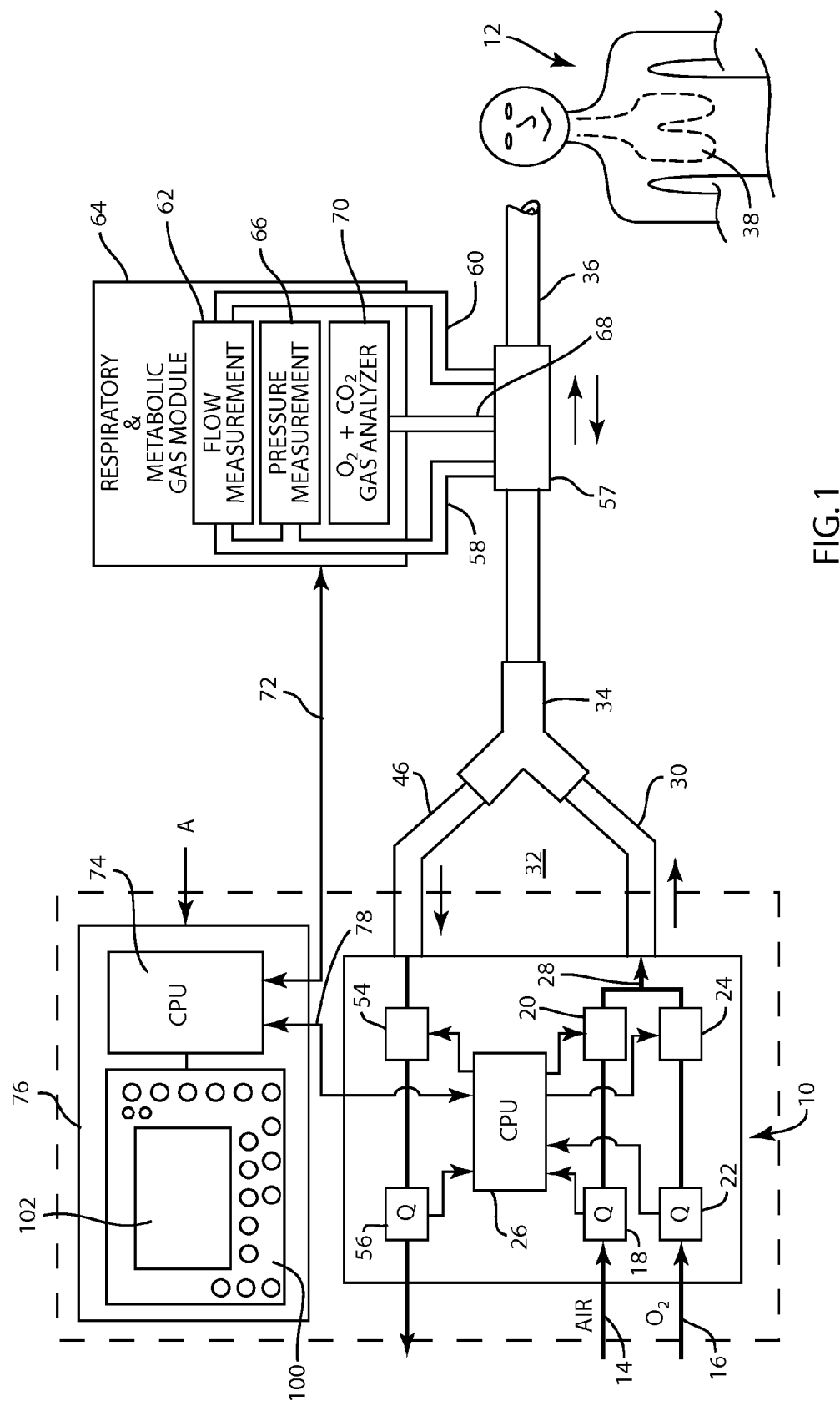
FIG. 1 is a general diagram of a mechanical ventilator and associated apparatus for ventilating a patient.

FIG. 1 shows mechanical ventilator 10 for providing breathing gases to patient 12. Ventilator 10 receives air in conduit 14 from an appropriate source, not shown, such as a cylinder of pressurized air or a hospital air supply manifold. Ventilator 10 also receives pressurized oxygen in conduit 16 also from an appropriate source, not shown, such as a cylinder or manifold. The flow of air in ventilator 10 is measured by flow sensor 18 and controlled by valve 20. The flow of oxygen is measured by flow sensor 22 and controlled by valve 24. The operation of valves 20 and 24 is established by a control device such as central processing unit 26 in the ventilator.

The air and oxygen are mixed in conduit 28 of ventilator 10 and provided to inspiratory limb 30 of breathing circuit 32. Inspiratory limb 30 is connected to one arm of Y-connector 34. Another arm of Y-connector 34 is connected to patient limb 36. During inspiration, patient limb 36 provides breathing gases to lungs 38 of patient 12. Patient limb 36 receives breathing gases from the lungs of the patient during expiration. Patient limb 36 may include components such as a humidifier for the breathing gases, a heater for the breathing gases, a nebulizer, or a water trap (not shown). The breathing gases expired by patient 12 are provided through patient limb 36 and Y-connector 34 to expiratory limb 46 of breathing circuit 32. The expired breathing gases in expiratory limb 46 are provided through valve 54 and flow sensor 56 for discharge from ventilator 10. Valve 54 may be used to establish the PEEP for patient 12.

Patient limb 36 includes gas flow and pressure sensor 57 which may be of the type shown in U.S. Pat. No. 5,088,332. A pair of pressure ports and lines 58, 60 are placed on either side of a flow restriction in the sensor and the pressure difference developed across the flow restriction is used by flow measurement unit 62 in gas module 64 to measure gas flow in patient limb 36. One of the pressure lines is connected to pressure measurement unit 66 to measure the pressure in patient limb 36. Sensor 57 also provides for a gas sampling line 68 which is connected to gas analyzer 70. Gas analyzer 70 may measure the amount of oxygen and carbon dioxide in the breathing gases. Knowing the amounts of oxygen and carbon dioxide in the breathing gases enables the amount of nitrogen to be determined as the total amount of the breathing gases less the amounts of carbon dioxide and oxygen. Respiratory and metabolic gas module 64 may comprise that made and sold by GE Healthcare as a Datex-Ohmeda MCOVX gas module. The output of gas module 64 is provided in data bus 72 to central processing unit 74 in ventilator display unit 76. Central processing unit 26 in ventilator 10 is also connected to central processing unit 74 via data bus 78.

The Endotracheal Tube

Figure 2:
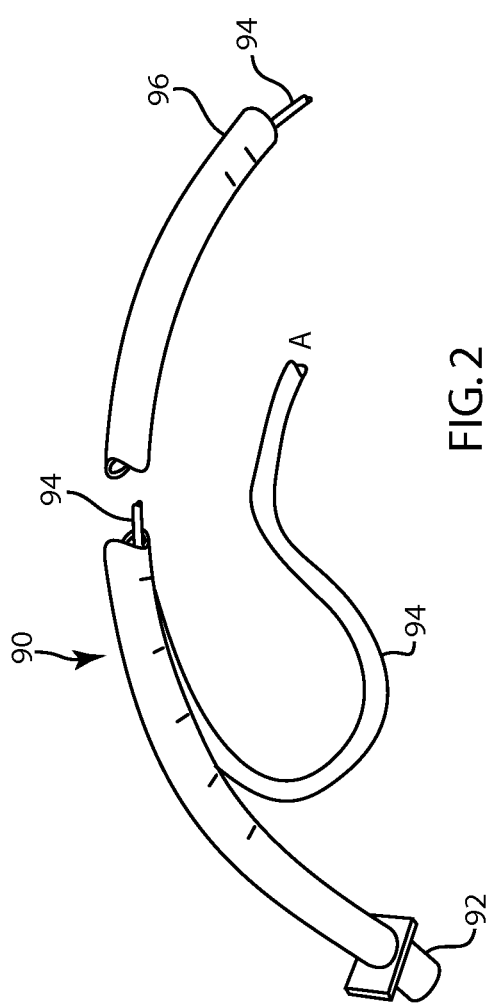
FIG. 2 shows an endotracheal tube with a tracheal pressure sensor suitable for use in the present invention.

To obtain an accurate indication of the pressure in lungs 38 of the patient 12, endotracheal tube 90 shown in FIG. 2 may be used. Endotracheal tube 90 has end 92 for connection to patient limb 36. In use, endotracheal tube 90 extends through the mouth and into the trachea of patient 12 to provide an airway passage to lungs 38.

Endotracheal tube 90 includes pressure sensor catheter 94 that extends from end 96 to provide a pressure sampling point that is close to lungs 38 of patient 12 when the endotracheal tube is inserted in the patient and can thus obtain a highly accurate indication of the pressure in the lungs. An intermediate portion of catheter 94 may lie within endotracheal tube 90. The proximal portion exits the endotracheal tube and is connected via A-A to a pressure transducer and to an auxiliary input to ventilator display unit 76. The pressure obtained from catheter 94 is termed Paux. While FIGS. 1 and 2 show a connection to ventilator display unit 76 for this purpose, the connection may, alternatively, be to gas module 64.

An endotracheal tube of the type shown in FIG. 2 is described in U.S. Pat. No. 6,315,739.

Ventilator Display Unit

Display unit 76 of ventilator 10 receives information from the ventilator and gas module 64 and is used by the clinician to control, via data bus 78, the pneumatic control components of ventilator 10 that deliver breathing gases to patient. Additionally, central processing unit 74 in display unit 76 carries out the determination of functional residual capacity, recruited/de-recruited volumes, and other quantities employed in the present invention. It will be appreciated that other CPU configurations, such as a single CPU for the ventilator and its display unit may be used, if desired.

Ventilator display unit 76 includes user interface 100 and display 102. Display 102 is shown in greater detail in FIG. 3. Display 102 is divided into a number of display portions 102a-g for displaying inputted, sensed, and computed information. Display portions 102a though 102l relate primarily to the operation of ventilator 10 and the ventilation of patient 12 and are discussed briefly below. Display screen portion 102g displays information and relationships in accordance with the present invention, as described in detail below.

Display portion 102a provides for the display of operating information of ventilator 10. The portion shows the type of ventilation being performed by ventilator 10, in the exemplary case of FIG. 3, synchronized, intermittent, mandatory ventilation, or SIMV-volume controlled ventilation. Portion 102a also provides a display of operating information inputted into ventilator 10 including the percentage of oxygen for the breathing gases, tidal volume (TV), breathing rate, inspiration time ($T_{insp}$), amount of positive end expiratory pressure (PEEP) and the pressure limit ($P_{limit}$) set for the volume controlled ventilation. To input these operating parameters into ventilator 10, an appropriate one of buttons 104a through 104f is actuated. Control knob 106 is rotated to enter a desired value for the selected option and pressed to confirm the new parameter value. Further ventilator functions may be controlled by pressing a button that controls a specialized function such as ventilator setup button 73 that establishes other ventilation modes for patient 12, spirometry button 75 for showing and controlling the display of spirometry information, 100% $O_2$ button 77, nebulizer button 79, and procedures button 80 that controls specialized procedures for ventilator 10.

Display portion 102b of display 102 shows airway pressure data as measured from sensor 57. Portion 102c shows textual information relating to the flow of breathing gases to the patient obtained from sensor 57, and portion 102d shows pressure data from catheter 94 in the endotracheal tube 90 during ventilation of patient 12.

Portion 102e of display 102 shows the information in portions 102b, 102c, and 102d in graphic form and includes an indication of certain other operating information, such as the mode of ventilation SIMV-VC, and whether certain features of the present invention are operational or not.

Figure 3:
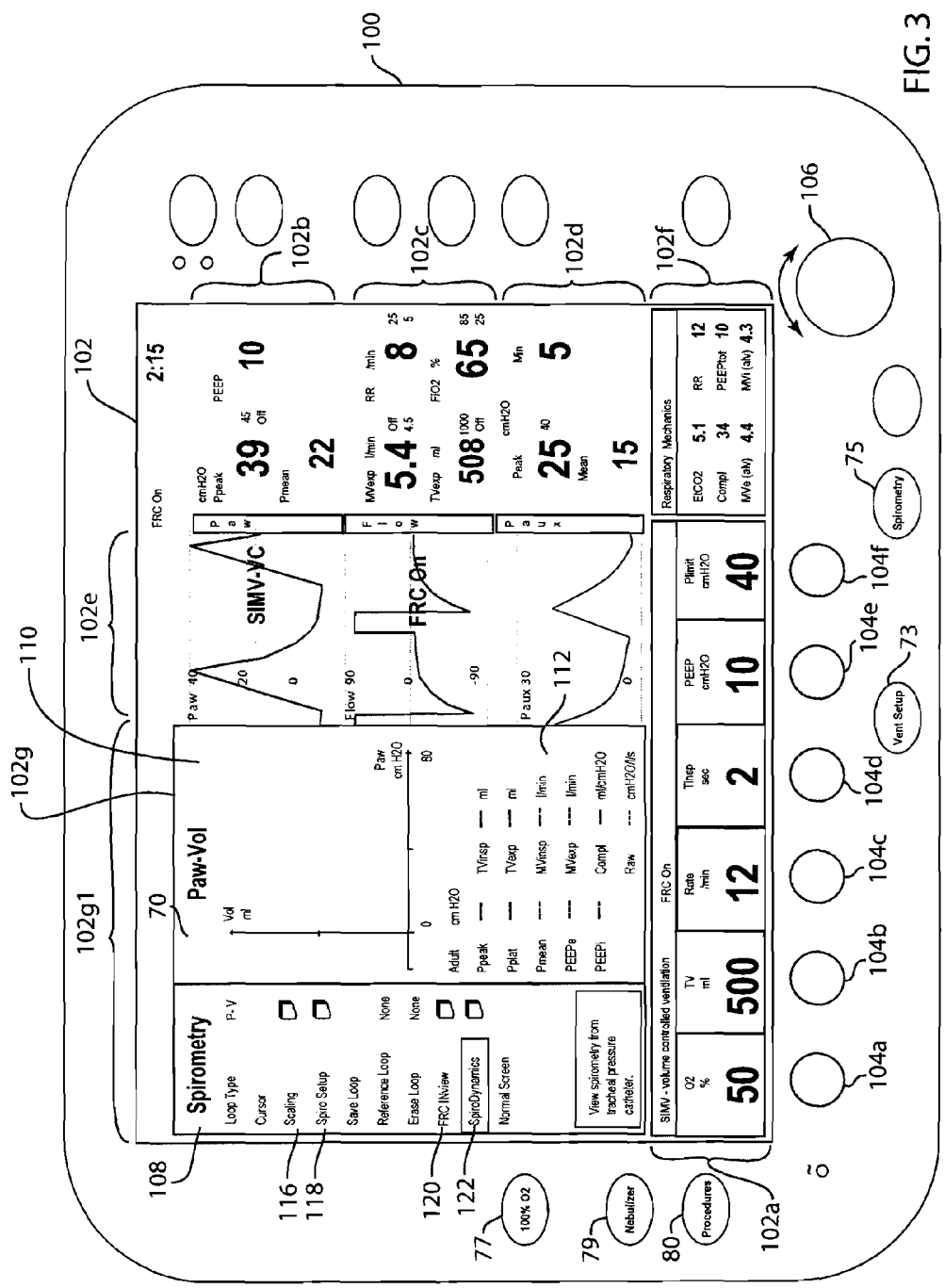
FIG. 3 shows a ventilator display unit presenting an initial display screen for use in the present invention.

Display portion 102f of display 102 shows additional data as selected by the clinician. In the example of FIG. 3 end tidal $CO_2$ ($E_1CO_2$), lung compliance, expiratory alveolar minute volume (MVe (alv)), respiratory rate, total positive end expiratory pressure, and inspiratory alveolar minute volume (MVi (alv)) are being shown.

Display portion 102a-f remain generally unchanged as the present invention is practiced although, as noted above, the clinician may select the information to be shown in certain portions, such as portion 102f.

Display Screen of Present Invention

Figure 4:
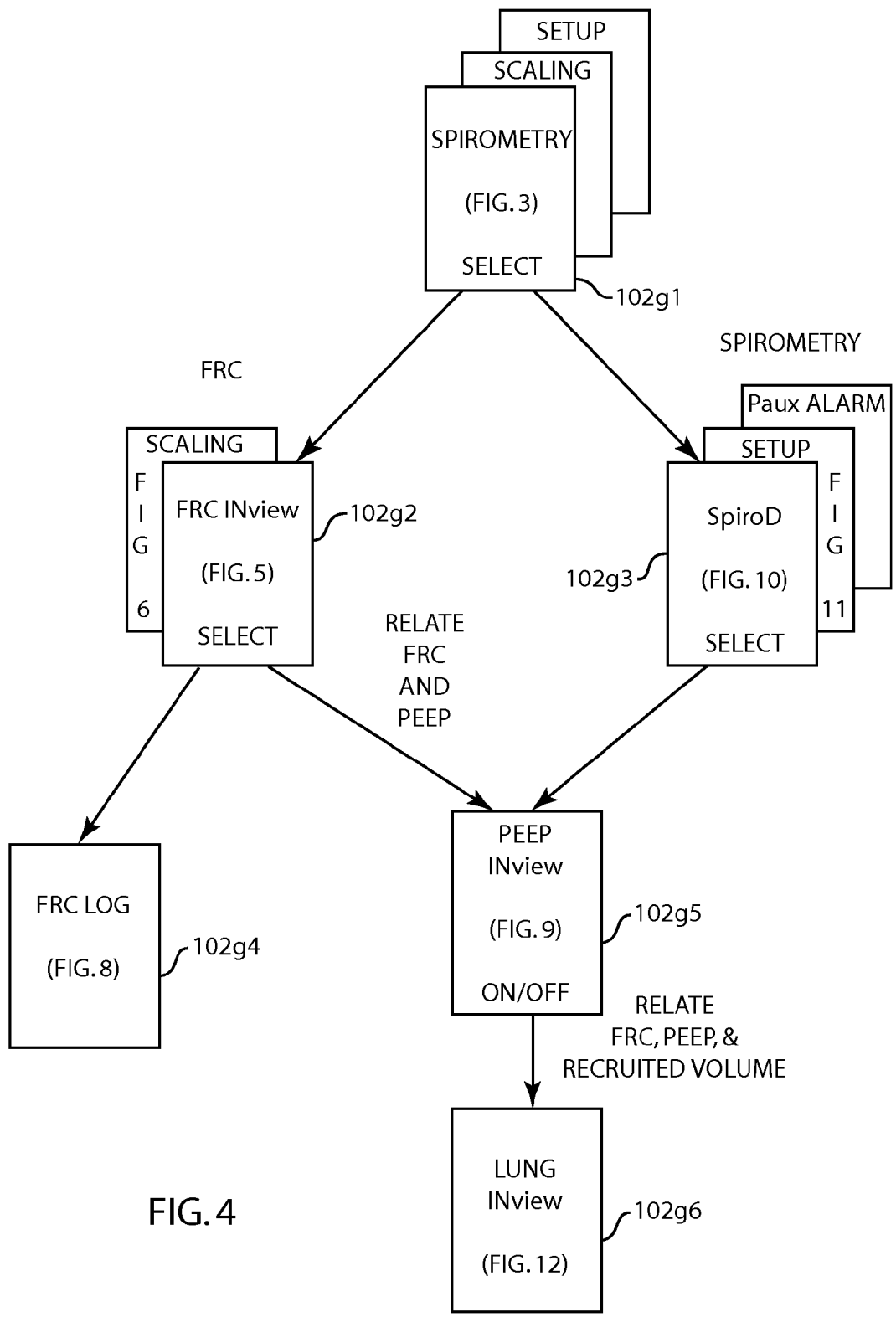
FIG. 4 is a chart showing the relationship among a plurality of screens employed in the present invention.

Display screen 102g is the part of display 102 employed in the present invention. As shown in FIG. 4 and in FIGS. 5, 6, 8 and 9-12, the content of this screen will change, depending on the inventive feature being utilized, the different content in screen 102g being identified as 102g1, 102g2, 102g3, etc. in the appropriate figures of the drawing.

In general, each screen 102g will include a menu or control portion 108, a graphic portion 110 and tabular portion 112. For this purpose, graphic portion 110 contains a pair of orthogonal axes by which data can be graphically presented. The clinician may navigate and control the screen using control knob 106. Control knob 106 is rotated to scroll through the menu options displayed in menu portion 108, depressed to select a menu option, rotated again to establish a numerical value for the selected option when appropriate, and depressed again to enter the value into ventilator display unit 76 or to confirm selection of the menu option.

FIG. 3 shows an initial content for screen 102g relating to spirometry. As hereinafter noted, spirometry illustrates the relationship between inspired gas volumes and the pressure in the lungs as the patient breathes. The graphic form of the data is normally in a loop, one portion of which is formed during inspiration and the other portion of which is formed during expiration in the manner shown in FIG. 10. The tabular portion 112 provides fields in which various obtained and computed ventilation and lung properties may be displayed.

Menu portion 108 allows the clinician to select a number of options with respect to the display and use of the information shown in graphic and tabular portions 110 and 112. Menu portion 108 also allows the clinician to select a further screen at 116 for adjusting the scaling for the abscissa and ordinate of graph 110 and the setup for spirometry measurements at 118.

From menu portion 108, the clinician may also select screens that allow the functional residual capacity (FRC) features of the present invention and the spirometry features of the present invention to be carried out by selecting items 120 and 122, respectively. The spirometry features of the present invention are identified by applicant as SpiroDynamics or the abbreviation SpiroD.

FIG. 4 shows the architecture of the screens 102g used in the present invention. As noted above, the spirometry screen shown in FIG. 3 as screen 102g1 is the initial screen appearing as screen 102g. Also as noted above, associated with this screen are screens for spirometry scaling and spirometry setup.

Figure 10:
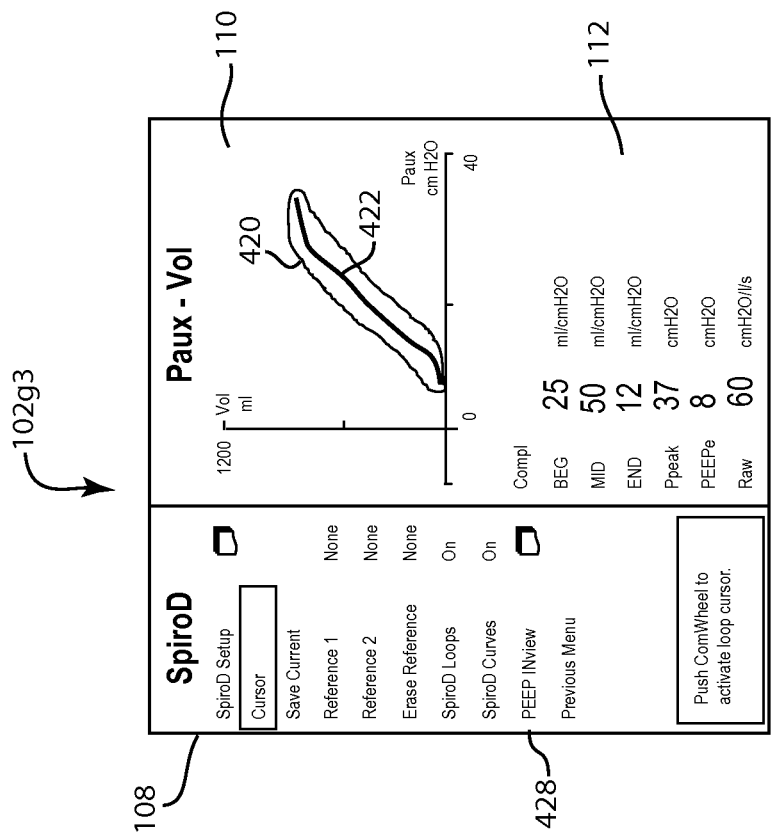
FIG. 10 shows a display showing spirometry data.

By means of menu items 120 and 122, the clinician can select either a screen relating to functional residual capacity, namely screen 102g2 shown FIG. 5 or a screen relating to SpiroDynamics comprising screen 102g3 of FIG. 10. The screen format of FIG. 5 is termed "FRC INview." The view of FIG. 10 is termed "spiroD".

The FRC INview showing of 102g2 includes screen shown in FIG. 6 that allows for scaling of the quantities shown graphically in FIG. 5.

A further selection on the FRC INview screen allows the clinician to select the FRC log screen shown in FIG. 8 as screen 102g4.

Selections on either of the FRC INview screen 102g2 or the SpiroDynamic screen 102g3 allows selection of a PEEP INview screen shown in FIG. 9 as 102g5. As hereinafter described, this screen allows the clinician to see the relationship between functional residual capacity and PEEP to assist in selecting an appropriate PEEP for patient 12.

Finally, an on/off selection option in PEEP INview screen 102g5 allows the clinician to display lung INview screen 102g6 shown in FIG. 12. The information contained in this screen relates functional residual capacity, PEEP, and recruited/de-recruited lung volumes to further assist the clinician in setting the appropriate level of PEEP.

FRC Determination and Display

The flow chart of FIG. 7 shows a method for determining and displaying functional residual capacity information for patient 12. The clinician uses a screen in the format of 102g2 of FIG. 5. It is assumed that the clinician has previously established an oxygen percentage for the breathing gases to be provided by ventilator 10 using button 104a, control knob 106 and screen region 102a, at step 200. In the example shown in FIG. 3, the oxygen percentage is 50%. Ventilator 10 can be operated with the set percentage of oxygen to provide breathing gases to patient 12 at step 202.

As noted above, in order to determine the functional residual capacity of patient 12 by a gas wash-out/wash-in technique, it is necessary to alter the composition of the breathing gases supplied to patient 12. To this end, the clinician sets a different level for the oxygen content of the breathing gases. This is performed by selecting the FRC $O_2$ field 206 in menu portion 108 of screen 102g2 and appropriately establishing the FRC $O_2$ value. The amount of change may be an increase or decrease from the previously set level established at step 200; however it must be an amount sufficient to perform the functional residual capacity analysis. A change of at least 10% is preferable in order to obtain an accurate indication of the functional residual capacity. To ensure that appropriate oxygen concentrations are supplied to patient 12 it is usually desired to increase the oxygen level and, unless the current oxygen level is very high (greater than 90%), a default setting of a 10% increase over the current setting may be provided. The level of oxygen set by the clinician "tracks" changes made in the oxygen content of the breathing gases at the ventilator, as for example by actuating button 104a. Thus, for example, if the ventilator oxygen is originally 50% as shown in FIG. 3, and the FRC 02 shown in FIG. 5 is 60%, if the ventilator oxygen setting is later changed to 70%, the FRC 02 amount will automatically move to 80%. Lowering the ventilator oxygen setting, however, will not result in lowering the FRC 02 amount, thereby avoiding the possibility of low oxygen breathing gases for the patient. The alteration of the oxygen content of the breathing gases is carried out in step 208 of FIG. 7. For exemplary purposes, below, an alteration in the form of an increase to 75% $O_2$ is shown in FIG. 5.

Next, the clinician must select the frequency, or interval, at which the functional residual capacity measurements will be carried out. This is performed at step 210. A single functional residual capacity determination by the present method may be selected by the appropriate field 212 in menu 108. Alternatively, a series of FRC determinations or cycles may be selected, with a series interval, set in field 214, between each determination. The interval may be between one and twelve hours in increments of one hour. The time when the next functional residual capacity determination begins is shown in field 215.

Alternatively, functional residual capacity measurements can be set to occur automatically in conjunction with certain procedures controlled by ventilator 10, such as immediately prior and/or after a period of nebulized drug therapy, recruitment maneuvers, a suction procedure, or a change in ventilator setting. Functional residual capacity measurement may be initiated, terminated, delayed, interrupted, or prevented in accordance with the occurrence of events, such as those noted above, that may affect the accuracy of the functional residual capacity measurement. For example, a functional residual capacity measurement may be terminated for a high oxygen procedure for patient 12 and then resumed or started after a "lock out" period.

The initial or base line amount of nitrogen in the expired breathing gases is determined at step 216. As noted above this may be determined by subtracting the amounts of oxygen and carbon dioxide, as determined by gas analyzer 70, from the total amount of the breathing gases, as determined using flow measurement unit 62.

While the present invention is described using nitrogen as the inert gas, it will be appreciated that other inert gas may also be used. For example, the breathing gases for patient 12 may include the inert gas helium and amounts of helium expired by the patient could be used in a functional residual capacity measure in the manner described herein.

To commence the determination of functional residual capacity, breathing gases having the increased amount of oxygen shown in data field 206 are provided to patient 12 in step 218. The increased percentage of oxygen in the breathing gases will wash a portion of the nitrogen or other inert gas out of lungs 38 of patient 12 with each breath of the patient. The amount of breathing gases inspired and expired by patient 12 with each breath, i.e. the tidal volume, is a lung volume that is in addition to the residual volume of the lungs found after expiration. The tidal volume is also smaller than the residual volume. For a healthy adult a typical tidal volume is 400-700 ml whereas the residual volume or functional residual capacity is about 2000 ml. Therefore, only a portion of the nitrogen in the lungs 38 of patient 12 is replaced by the increased amount of oxygen with each breath.

The amount of nitrogen washed out of the lungs in each breath is determined by subtracting the amount of oxygen and carbon dioxide from the amount of breathing gases expired by patient 12 during each breath obtained using flow measurement unit 62. See step 220. Knowing the amount of expired breathing gases, the initial amount of expired nitrogen and the amount expired in each expiration by patient 12, a functional residual capacity quantity can be determined for each successive breath in steps 222a, 222b . . . 222n. Any inert gas wash out/wash in functional residual capacity measurement technique may be used, a suitable technique for determining functional residual capacity for use in the present invention being described in U.S. Pat. No. 6,139,506.

The functional residual capacity quantity as determined after each successive breath, will tend to increase as nitrogen continues to be washed out of the lungs of the patient by the increased oxygen in the breathing gases. This results from the fact that the breathing gases that are inspired by patient 12, i.e., the tidal volume, are not fully equilibrated inside the entire functional residual capacity volume before being exhaled by the patient. In particular, functional residual capacity volume that lies behind intrinsic lung resistance does not mix as quickly with inspired gases compared to functional residual capacity volume that is pneumatically connected to the trachea through a lower resistance path. As such, the magnitude of breath-to-breath increases in functional residual capacity that are noted are an indication of the amount of intrinsic resistance within the lung gas transfer pathways. Thought of another way, additional functional residual capacity volume that is registered many breaths into the functional residual capacity measurement procedure is lung volume that is not participating well in the gas transfer process.

As the determination of functional residual capacity proceeds, the determined values for functional residual capacity for the breaths are displayed in graphic portion 110 of screen 102g2 as a capacity or volume curve 224 in steps 226a, 226b . . . 226n at the end of the determination for each breath. This confirms to the clinician that the determination of functional residual capacity is working properly. Also, as curve 224 forms from left to right, the shape of the curve is an indication to the clinician of the intrinsic resistance and quality of ventilation of lung functional residual capacity, as discussed above. In the example shown, the clinician can appreciate that patient 12 has a homogeneously ventilated lung volume, as indicated by the qualitative flatness of the functional residual capacity curve, with a lung residual capacity of about 2500 ml.

The scaling of graph 110 of FIG. 5 may be automatically altered to provide a scale appropriate to the functional residual capacity data being shown.

It will be appreciated that, if desired, the data relating breath number to the corresponding functional residual capacity value can also be displayed in tabular form in portion 112 of display portion 102g. This could comprise a column containing the breath numbers and a column containing the corresponding functional residual capacity values.

Mechanical ventilator 10 continues to supply breathing gases having increased oxygen concentration for x number of breaths, for example, 20 breaths. A final value for functional residual capacity is determined at the end of the x breaths at step 228 and volume or capacity curve 224 extends to this breath to show the final determination of functional residual capacity at the end of 20 breaths. The functional residual capacity measurement may conclude earlier if sufficient stability of breath-to-breath functional residual capacity is found in curve 224.

Thereafter, at step 230 the concentration of oxygen in the breathing gases is altered to the original level of, for example 50%, set at step 200 and ventilator 10 is operated at step 232 to repeat steps 216-228 to make a second determination of functional residual capacity with this alteration of the oxygen concentration in the breathing gases. It will be appreciated that this determination uses a wash-in of nitrogen, rather than a wash-out. This second determination is graphed and displayed in graphic portion 110 as graph 234, in the same manner as graph 224, described above. The values for the two final functional residual capacity determinations are shown in data field 237 of tabular portion 112 of screen 102g2 in step 236. In the example shown, these values are 2500 and 2550 ml.

For future use, the final determination of functional residual capacity made in step 232 is compared to that determined in step 228. This is carried out at step 238. It is then determined, in step 240, whether the difference between the two determinations of functional residual capacity is less or greater than some amount, such as 25%. If the difference is less than 25%, the two values are averaged and will be subsequently displayed in text form in data field 245 in step 244 when determination becomes part of the chronological record following a later functional residual capacity determination.

If the difference between the two values for the functional residual capacity is greater than some amount, such as than 25%, both the final value determined at step 228 and the final value determined in step 232 will be displayed by step 246 in data field 245 of FIG. 5 and in the graph 110. This display of the functional residual capacity determination informs the clinician that the accuracy of the functional residual capacity determination is questionable.

The final value(s) for the functional residual capacity are preferably displayed in tabular portion 112 of screen 102g2 along with additional associated data such as the time and date at which functional residual capacity was determined, or the values of PEEPe and PEEPi existing when the functional residual capacity determination was made. PEEPe is the end expiratory pressure established by ventilator 10. PEEPi, also known as auto PEEP, is the intrinsic end expiratory pressure and is a measurement in pressure of the volume of gas trapped in the lungs at the end of expiration to the PEEPe level.

While the determination of functional residual capacity has been described as being carried out for a given number of breaths, such as 20, it can be terminated sooner if it is apparent that the functional residual capacity measurement has become stable on a breath-to-breath basis. This can be conveniently determined by measuring the $O_2$ content of the expired breathing gases at the end of the patient's expirations, that is, the end tidal oxygen level. When the amount of oxygen in the expired breathing gases attains and remains at the altered level, it is an indication that the wash out/wash in the inert gas is complete and that the functional residual capacity determination can be terminated.

Thereafter, if a series of functional residual capacity determinations has been selected at step 210, steps 218 through 246 are repeated after the time interval indicated in data field 214 with the start of the functional residual capacity determination occurring at the time displayed in data field 215. The predetermined time interval may be overridden or the functional residual capacity determination terminated by appropriate commands from the clinician entered into menu 108.

The volume curves, such as 224, 234, and functional residual capacity data, such as that in field 237, generated in the course of successive functional residual capacity determinations are saved by ventilator display unit 76 and, as such, can be compared to data from previous or subsequent functional residual capacity determinations. This comparison requires that a previous determination of functional residual capacity be selected as a reference curve using the time at which it was obtained as identified in data field 250. When a reference curve is selected, an indication is made in data field 250 and that functional residual capacity curve is displayed as the reference curve 252. Curve 252 shows a lung that is not well ventilated. Further indication of the reference curve and reference curve values may be made by a color indication for this data, different from that of the other functional residual capacity data in graph 110 and table 112. The result is a visual indicator that can easily be referred to by the clinician to quickly assess improvement or deterioration in the functional residual capacity condition of patient 12 over time. In the example shown in FIG. 5, there has been an increase in the functional residual capacity of patient 12 for each eight hour interval.

Also, it is common practice to alter, usually increase, the PEEP to improve ventilation of lungs 38 of patient 12 by opening areas of the lung that are not being properly ventilated. Tabulating the actual measured values for PEEPe and PEEPi, along with the corresponding functional residual capacity determination, as shown in FIG. 5, allows the clinician to see the effect, if any of applied PEEPe therapy on the volume of the functional residual capacity of the patient's lungs, as well as on the intrinsic PEEP. As also shown in FIG. 5, a history of a certain number of functional residual capacity determinations and PEEP pressures are shown in table 112 to present trends and the history of these quantities. In the example shown there, an increase in PEEPe has resulted in an increase in functional residual capacity of patient 12.

FRC Events Log

Certain clinical or other events can affect the value for functional residual capacity determined from the method steps shown in FIG. 7. Such events may include performing a suction routine on patient 12 to remove accumulated secretions, administering a nebulized medication, changing the ventilation mode, or changing one or more ventilation parameters, such as tidal volume (TV), breath rate, PEEP, or other parameter.

By selecting the FRC Log field 253 in menu 108 of screen 102g2 shown in FIG. 5, screen 102g4 of FIG. 8 will be shown to provide a log of the events that may effect functional residual capacity in data field 254 along with the time(s) and date(s) the event took place. The log also includes the time, date and value of any periodic functional residual capacity determinations made in the manner described above. The clinician may scroll through the events of the log using control knob 106 to review the functional residual capacity event history in relation to the measured values of functional residual capacity to determine if specific actions had a positive or negative effect on the determined functional residual capacity for the patient.

PEEP Determination and Display

An aspect of the present invention allows the clinician to ascertain the relationship between the functional residual capacity of patient 12, and PEEP applied to the patient, thereby to assist the clinician in establishing a PEEP level deemed optimal for patient 12. An optimal PEEP level, in the present context, is one beyond which diminishing functional residual capacity increases in association with PEEP increases are noted. The PEEP INview screen 102g5 of FIG. 9 may be used for this purpose. For screen 102g5, a series of periodic functional residual capacity determinations is made, preferably in the manner shown in FIG. 7, with each determination being at a different incremented level of PEEP. For this purpose, in menu 108, the clinician sets an altered concentration of oxygen to be used in the functional residual capacity determination in data field 400. The clinician also enters an initial PEEP value at data field 402 and an end PEEP value at data field 404. The initial PEEP value may be low and the end value high, as shown in FIG. 9, or the initial value high and the end value low. The clinician also sets the number of functional residual capacity measurements to be made between the initial and end PEEP values in data field 406. In the example shown in FIG. 9, five such measurements are to be made. In an alternative embodiment, the incremental PEEP associated with each measurement, for example an incremental change of 3 $cmH_2O$ for each measurement, may be set. While use of the method of determining functional residual capacity of FIG. 7 is described below, it will be appreciated, that for the purpose of determining a suitable PEEP, any method of determining functional residual capacity may be employed.

The series of measurements of functional residual capacity starting at the initial value of PEEP and incrementally moving to the end value of PEEP is then performed as in a manner of steps 216-228 or steps 216-246 shown in FIG. 7. These functional residual capacity determinations are graphically displayed in graph 110 of FIG. 9 as points/curve 408. Graph 110 of screen 102g5 has functional residual capacity on the ordinate and PEEP on the abscissa. The corresponding numeric functional residual capacity data is displayed in table 112 that contains the functional residual capacity values and the PEEP values at which that functional residual capacity value was obtained.

Curve 408 and table 112 provide guidance to the clinician in selecting a PEEP level for ventilating patient 12. For example, from the graph and table of FIG. 9 it can be seen that increasing the PEEP from 2 to 6 $cmH_2O$ increases functional residual capacity by 500 ml whereas increasing PEEP beyond 6 $cmH_2O$ provides a relatively small increase in functional residual capacity. This suggests to the clinician that 6 $cmH_2O$ would be an appropriate PEEP for the patient.

Curve 408 can be saved in a memory in ventilator 10 or display unit 76. If ventilator settings are not changed or are not changed in any significant way, curves 408 obtained at different times in the course of the patient's treatment can be usefully presented in graphic portion 110 of screen 102g5 to enable the clinician to note changes in the PEEP curve over time by comparing the data of two or more curves 408 over time.

Also, while the foregoing has described obtaining and presenting a graph and table of functional residual capacity and PEEP, other aspects of the ventilation of patient 12 by ventilator 10 may affect the functional residual capacity. For example, the respiration rate, or the related quantities of expiration time and inspiratory:expiratory (I:E) ratio, can affect functional residual capacity primarily through the mechanism of intrinsic PEEP. Determining and displaying the relationship of one or more of these quantities to functional residual capacity may be useful to a clinician. To this end, the functional residual capacity of the lungs 38 of patient 12 can be determined at differing respiration rates and the data displayed in graphic or tabular form to show the relationship between functional residual capacity and respiration rate. In graphic portion 110, the abscissa would show the respiration rate while the ordinate continues to show functional residual capacity. A tabular presentation comprises a column of respiration rates and a column of corresponding functional residual capacity determinations.

Figure 9B:
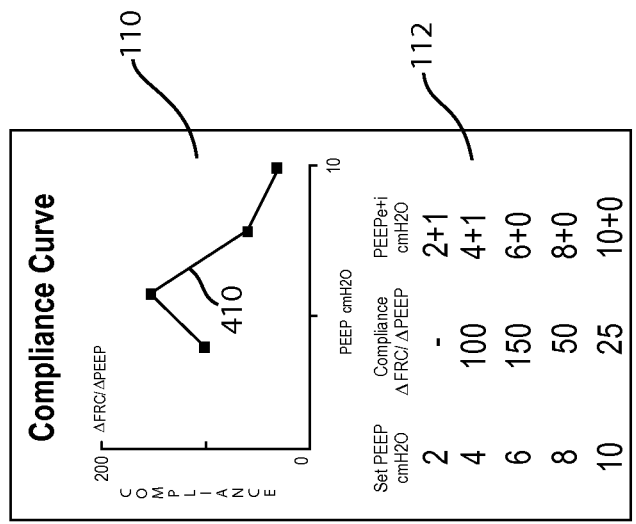
FIG. 9B shows a display showing the relationship of changes in PEEP to corresponding changes in functional residual capacity.

FIG. 9B shows an example of a further manner of obtaining and displaying functional residual capacity and PEEP data. In FIG. 9B, the abscissa presents PEEP and the ordinate presents the change in functional residual capacity volume for a given change in PEEP, or $\Delta FRC/\Delta PEEP$.

The relationship between changes in lung volume and changes in lung pressure is termed the "compliance" of the lung. As a general expression of lung characteristics, it describes the elasticity or "stiffness" of the lungs. Lungs of high compliance are elastic and a large change in volume occurs for a small change in pressure. The reverse is true for a stiff lung. Some lung conditions decrease lung compliance. Others, such as emphysema, increase lung compliance.

In the present context, the presentation of changes in functional residual capacity volume, $\Delta FRC$, to changes in PEEP, $\Delta PEEP$, in FIG. 9B as compliance properties of the lung serves to emphasize clinically important data presented in graphic and textual form in FIG. 9 and to aid the clinician in selecting an appropriate PEEP for the patient. For this purpose, the ordinate of graph 110 in FIG. 9B is labeled as compliance. The data in FIG. 9 presented in the manner of FIG. 9B shows that the incremental 2 $cmH_2O$ pressure increase in PEEP from 2 to 4 $cmH_2O$ PEEP produced a functional residual capacity volume increase of 200 ml, giving a compliance of 100 $ml/cmH_2O$, as graphically shown in FIG. 9B at the left hand point of curve 410 in the graph. In the same manner, the incremental 2 $cmH_2O$ PEEP increase from 4 to 6 $cmH_2O$ PEEP produced a functional residual capacity volume increase of 300 ml, giving a compliance of 150 $ml/cmH_2O$ at the second point, proceeding to the right in the graph of FIG. 9B. Corresponding determinations are made for the incremental PEEP increases from 6 to 8 and from 8 to 10 $cmH_2O$ and shown by the remaining points of curve 410 in FIG. 9B. The data may also be presented in tabular form in table 112 of FIG. 9B.

The peak in the graph of FIG. 9B suggests to the clinician that a PEEP of 6 $cmH_2O$ would be advantageous for the patient.

Recruitment/De-Recruitment of Lung Volume

While screen 102g5 of FIG. 9 provides valuable insight and information to the clinician, it may also be helpful for the clinician to have a better idea of how much of an increase in functional residual capacity is due to distension of the lung by increased PEEP and how much is due to making previously closed alveolar sacs available, i.e., opening of the lung by "recruitment" of lung volume.

One way such information may be obtained using the PEEP INview screen 102g5 of FIG. 9 is as follows. Functional residual capacity is determined for a series of PEEPs, in the manner described above to produce a curve, such as curve 408. Thereafter a recruitment maneuver is carried out on patient 12 to open the alveolar sacs of the lungs of the patient. This would ordinarily be the provision of a high level of PEEP that, while it may only be tolerated by a patient for a short period of time, serves to open the alveolar sacs of the patient lungs. This is ordinarily carried out by the clinician by operating ventilator 10 independently of screen 102g5. For this maneuver, it is preferable to use a recruitment PEEP greater than the highest PEEP set in menu 108 of screen 102g5 to ensure the alveolar sacs open.

Figure 9A:
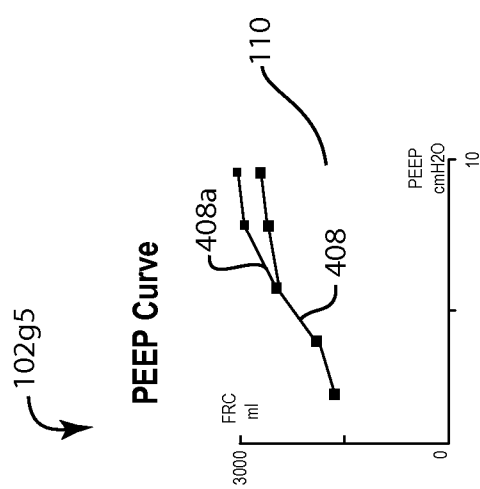
FIG. 9A shows a display showing changes in PEEP and functional residual capacity before and after a recruitment maneuver.

After the recruitment maneuver has been completed, the functional residual capacity is again determined for the same series of PEEPs used prior to performing the recruitment maneuver to produce another curve 408a. The two curves can be displayed in graphic portion 110 of screen 102g5 in the manner shown in FIG. 9A. If the recruitment maneuver resulted in the recruitment of lung volume, i.e. in the opening of previously closed alveolar sacs, curve 408a will show a higher functional residual capacity than curve 408, as shown in FIG. 9A. Curves 408 and 408a will tend to come together at the PEEP level at which de-recruitment of lung volume begins to occur. This suggests to the clinician that a PEEP level greater than one at which de-recruitment begins to occur would be appropriate for the patient.

Another way such information can be obtained is by using the spirometry aspects of the present invention, as shown in the SpiroD screen 102g3 of FIG. 10 and, particularly, the lung INview screen 102g6 of FIG. 12.

In general, spirometry is used to determine the mechanics of a patient's lungs by examining relationships between breathing gas flows, volumes, and pressures during a breath of a patient. A commonly used relationship is that between inspired/expired breathing gas flows and volumes that, when graphed, produces a loop spirogram. The size and shape of the loop is used to diagnose the condition of the lung.

A relationship also exists between inspired/expired gas volumes and pressure in the lungs. In the past, a problem with the use of this relationship has been that pressure has been measured at a point removed from the lungs so that the measured pressure may not be an accurate reflection of actual pressure in the lungs thus lessening the diagnostic value of the pressure-volume loop. Through the use of catheter 94 extending from endotracheal tube 90 shown in FIG. 2, a far more accurate indication of lung pressure is obtained. For a healthy lung, a graph of the relationship between volume and pressure is roughly an elongated, narrow loop of positive uniform slope. That is, constant increments of inspired volume increase lung pressure by constant increments. The loop is formed because there remains some amount of lung resistance below the pressure sensing point at the end of catheter 94. In a diseased lung, the loop may be wider and may also reflect a non-linear lung volume pressure relationship. For such a lung, the volume-pressure relationship over the course of an inspiration/expiration may be in a form such as that shown in FIG. 10 by 420, and a curve illustrating the volume-pressure relationship resulting from a mathematical computation using loop data is plotted, as shown in FIG. 10 by reference numeral 422. The curve 422 shown in FIG. 10 in often termed a "dynostatic curve" and is used for diagnostic purposes. A typical dynostatic curve is shown in FIG. 10 to contain a middle portion of somewhat linear positive slope and a pair of inflection points separating end portions of differing slopes. The dynostatic curve and its generation is described in Practical Assessment of Respiratory Mechanics by Ola Stenqvist, British Journal of Anesthesia 91(1), pp. 92-105 and "The Dynostatic Algorithm in Adult and Paediatric Respiratory Monitoring" by Soren Sonderguard, Thesis, University Hospital, Gothenburg University, Sweden (2002).

In graph 110 of FIG. 10, the abscissa of the graph is lung pressure measured at the end of catheter 94 connected to the auxiliary input A of ventilator display unit 76 and is termed "Paux". The ordinate is scaled in volume of breathing gases inspired/expired by patient 12. It will be appreciated that this volume comprises the tidal volume for the patient. The tidal volume moves into and out of the lungs in a manner that can be described as being "above" the functional residual capacity. That is, for normal breathing, a patient starts a breath with the volume of the lungs at the functional residual capacity which may, for example be 2000 ml. During inhalation, the volume of the lungs increases by the tidal volume of, for example 500-700 ml, and during exhalation, the volume of the lungs decreases by approximately that amount. The same situation occurs when a patient is being provided with breathing gases from a mechanical ventilator, such as ventilator 10. It must thus be appreciated that the ordinate of the graph 110 in FIG. 10 is scaled in the relative volume of inspiration/expiration for which the origin of the graph is zero, not in absolute volume that would also take into consideration functional residual capacity and for which the origin of a graph would be the amount of the functional residual capacity. The scaling of graph 110 of FIG. 10 may be automatically altered to provide a scale appropriate to the spirometry data being shown.

With PEEP applied to patient 12 by ventilator 10, there will be a movement of the graph away from the origin of the axes along the abscissa. The graph will move right by the amount or the PEEP, i.e. the lung pressure at the end of expiration by patient 12.

Figure 11:
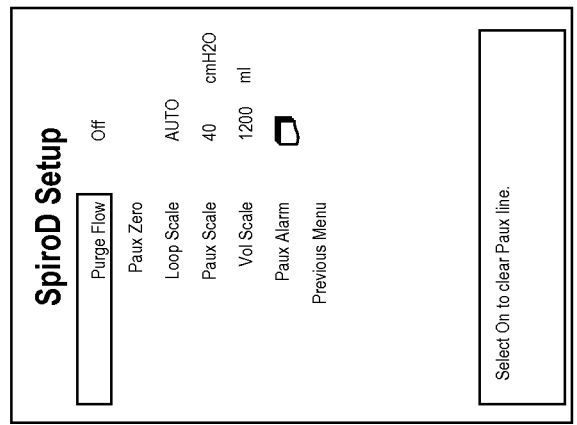
FIG. 11 shows a display for making setup adjustments for the screen shown in FIG. 10.

The menu portion 108 of SpiroD screen 102g3 shown in FIG. 10 allows the user to open up a set up menu, shown in FIG. 11 that allows the clinician to turn a purge flow through catheter 94 on or off or to zero the Paux sensor connected to catheter 94 when the purge flow is on and endotracheal tube 90 has been inserted in patient 12. The SpiroD set-up menu also allows the clinician to set the scaling for the graphical portions of the display. A "Paux Alarm" screen, reached from the SpiroD setup screen of FIG. 11, allows the clinician to set appropriate alarms for patient lung pressure, as sensed by catheter 94.

Various other selections on menu 108 of screen 102g3 of FIG. 10 allow the clinician to save the current data and to view this information as a first or second reference for use and display with subsequently obtained data. Up to a given number of loops, for example, six loops and curves, may be saved for analytical purposes. The "erase reference" option allows the user to determine which information to save and which to delete.

The "SpiroD loops" and "SpiroD curves" menu items may be turned on or off. Selecting "on" for both the curve and loop will display both the loop and the curve at once in the manner shown in FIG. 10. For easier comparison among loops and curves obtained at various times, either the loop or curve showing may be turned "off." The "cursor" option allows the clinician to scroll along the horizontal axis and display the actual pressure and volume measurements associated with the loops or curves that are displayed.

For the graphical showing of graph 110 of the screen 102g3 in FIG. 10, volumes and pressures are obtained from sensor 57 and catheter 94 and the spirometry data, computed and displayed for every third breath if the respiratory rate is less than some desired number, for example, 15 breaths per minute. If the respiratory rate is greater than that number, every fifth breath used. The loop 420 for a complete inspiratory/expiratory breathing cycle is displayed in the graph of screen 102g3 of FIG. 10. The dynostatic curve 422 is then calculated for display in graph 110.

Various compliance values for the patient's lungs are shown in the table 112 of screen 102g3 of FIG. 10. Compliance can be seen as the amount by which the volume of the lung increases for an incremental increase in lung pressure. The data necessary to determine compliance can be obtained from sensor 57 and gas module 64. Compliance is represented by the slope of dynostatic curve 422. It is an indication of the stiffness or elasticity of the lung. In a stiff lung, an incremental increase in pressure results in a smaller increase in volume over a lung that is more elastic and the slope of curve 422 is more horizontal. In an elastic lung, the reverse is true. To aid the clinician in analyzing the lungs of patient 10, the compliance is computed at the beginning, middle, and end of the respiratory cycle of the patient. As shown in the example in FIG. 10, the middle portion of dynostatic curve 422 indicates a portion of greater compliance than the end portions. This is reflected in the greater slope of the middle portion over those of the end portions. The table of the screen sets out numerical values. Ordinarily, the highly compliant, middle portion of curve 422 shown in FIG. 10 is that in which the lung is most effectively ventilated.

The table 112 of display 102g3 of FIG. 10 also shows the peak pressure achieved in the lungs during the breath, the PEEP pressure, and the airway resistance, Raw. The airway resistance is the pressure drop experienced by breathing gas flow of the lungs and is expressed in units of pressure per unit of flow. Airway resistance can also be determined with data from sensor 57 and gas module 64 in a manner described in the Stenqvist reference noted above.

Figures 12A, 12B:
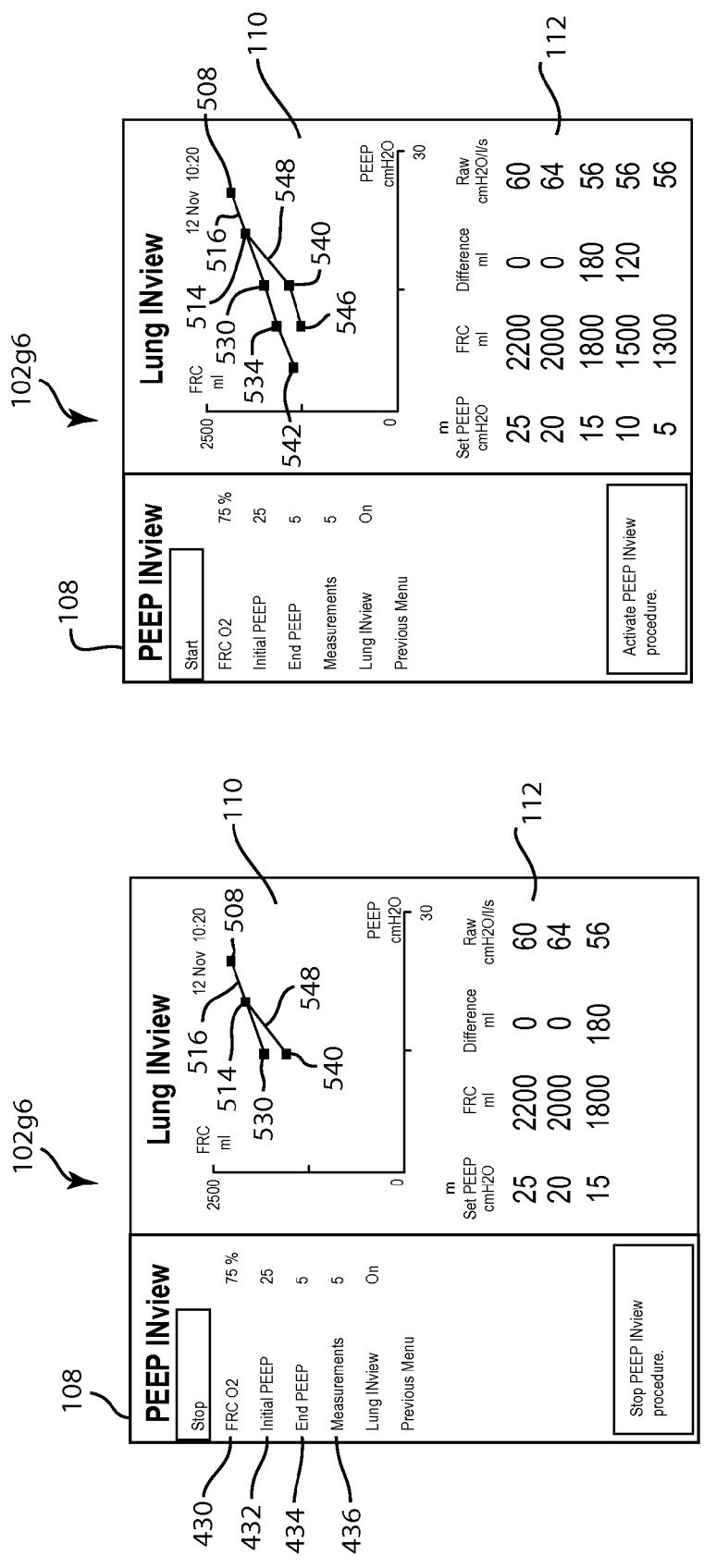
FIGS. 12a and 12b show a display showing relationships among functional residual capacity, PEEP, and recruited lung volume.

The present invention provides a unique way of viewing the relationship among functional residual capacity, PEEP, and recruited:de-recruited lung volume that is deemed helpful in enabling a clinician to determine a suitable value for PEEP. To carry this out, the PEEP INview screen 102g5 shown in FIG. 9 is reached. Among the menu items present in PEEP INview screen 102g5 is "Lung INview on/off" in field 424. When "Lung INview" is turned "on" a screen 102g6 in the format of FIGS. 12a and 12b is present in ventilator display unit 76. As shown in FIG. 4, the PEEP INview screen 102g5 of FIG. 9 can be reached either via the FRC INview display 102g2 described above and shown in FIG. 5 at field 426 or the SpiroD display 102g3 shown in FIG. 10 at field 428. When the former route is chosen to reach the PEEP INview screen of FIG. 9, the spirometry data described above will still be obtained and calculated in ventilator display unit 76 but the screen of FIG. 10 will not be displayed in the display unit.

To proceed with the Lung INview display, in the PEEP INview screen 102g5 shown in FIG. 9, the menu item "Lung INview on/off" 424 is toggled "on" and the ventilator display unit will show screen 102g6 in the format of FIGS. 12a and 12b.

For an embodiment of the invention using a wash in/wash out determination of functional residual capacity, in field 430 of menu 108 of display 102g6 of FIG. 12a/b, the clinician sets the altered oxygen level to be used in the functional residual capacity measurement employed to produce the Lung INview data. To begin the process of providing data for display 102g6, the clinician establishes initial and end PEEPs values at fields 432 and 434, as well as the number of measurements to be taken within the range of PEEP so established at field 436, in the same general manner as described above in connection with the PEEP INview display 102g5 of FIG. 9. Alternatively, and if desired, field 436 can show the incremental/decremental PEEP step, for example a step of 3 $cmH_2O$. In the example shown in FIG. 12, the initial PEEP is 25 $cmH_2O$, the end PEEP is 5 $cmH_2O$, and five measurements will be taken within that range of PEEP, namely measurements at 25, 20, 15, 10, and 5 $cmH_2O$ of PEEP. It is deemed preferable to initiate the process of determining the optimal PEEP by using the highest value of the selected range and thereafter decrementing the applied PEEP to the lower end level. However, as noted in connection with the description of screen 102g5 of FIG. 9, the invention can also be practiced with incrementing PEEP from a low value to a high value, depending on the preference of the clinician.

The graph 110 of screen 102g6 of FIG. 12 has the abscissa scaled in PEEP and the ordinate scaled in functional residual capacity. The table 112 of screen 102g6 provides columns for the set PEEP, functional residual capacity and airway resistance (Raw). The table also includes a column for "difference" that, as hereinafter described, contains a numerical indication of the lung volume that is recruited/de-recruited in the lungs as the PEEP is incremented/decremented.

Figure 13:
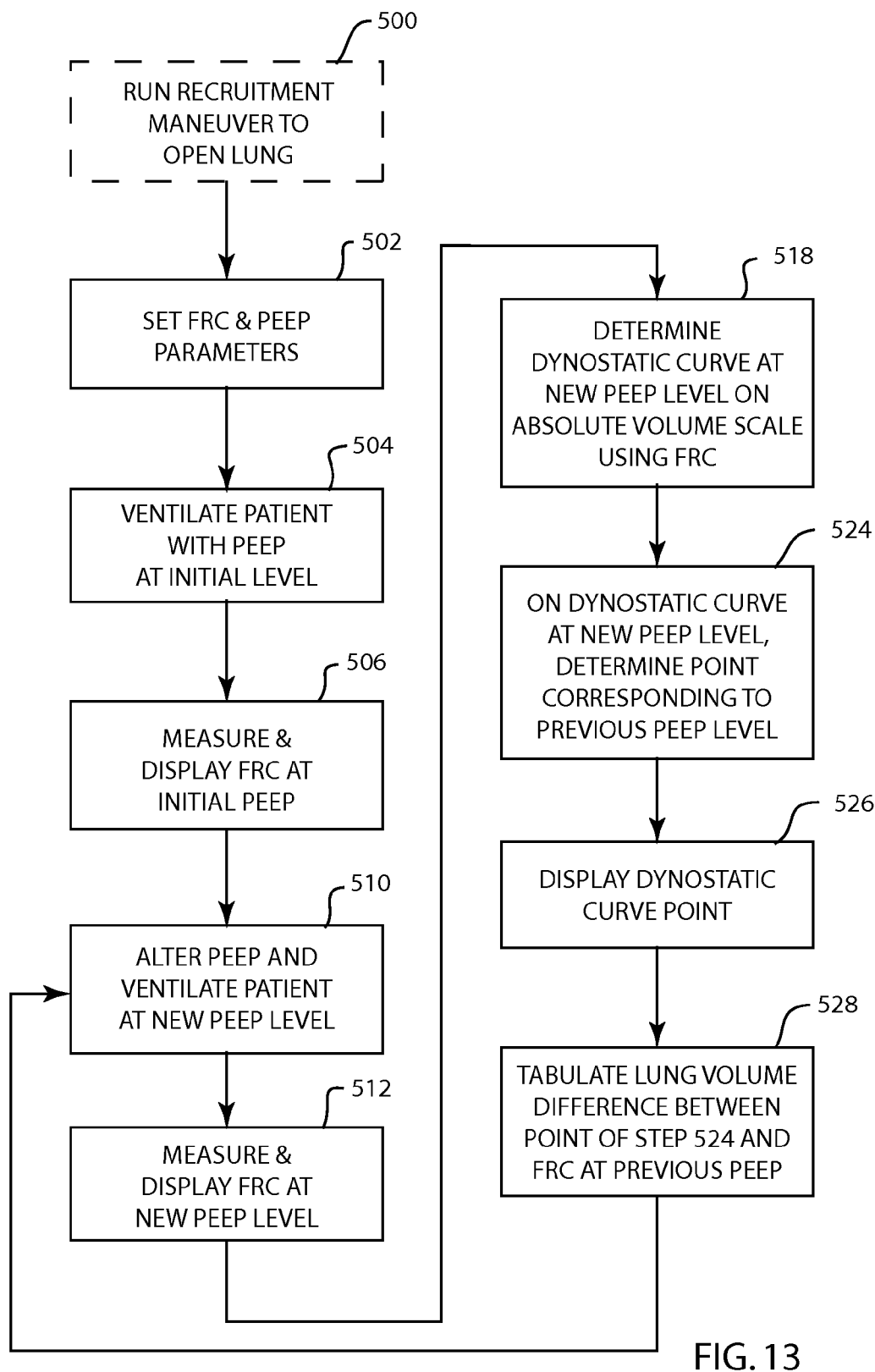
FIG. 13 is a flow chart showing the steps for carrying out a method for obtaining the relationships shown in FIGS. 12a and 12b.

As shown in FIG. 13, at step 500, a recruitment maneuver is preferably run on patient 12 to open the lungs of the patient. As noted above, such recruitment maneuver would typically be the provision of a high level of PEEP opens the alveolar sacs of the patient lungs. It is preferable to use a recruitment PEEP greater than the highest PEEP set in menu 108 of screen 102g6 to ensure the alveolar sacs open. In step 502, the functional residual capacity and PEEP parameters are established in menu 108 of display 102g6, shown in FIG. 12, as previously described. Step 502 may occur before step 500 reversing the order shown in FIG. 13. Thereafter, in step 504, the patient is ventilated by ventilator 10 with the PEEP at the initial level found in the menu. In the present exemplary instance, patient 12 is initially ventilated with a PEEP of 25 $cmH_2O$ in step 504.

In step 506, the functional residual capacity of patient 12 is determined by the wash in/wash out technique using the altered oxygen concentration level as described above in connection with FIGS. 5 and 7 or using some other appropriate technique for measuring functional residual capacity. The determined value is graphically displayed in graph 110 at the corresponding value of PEEP as point 508. The values are also entered in tabular form in table 112 of screen 102g6 of FIG. 12.

Next, the PEEP pressure is altered to the next decremental level, in the present instance from 25 $cmH_2O$ to 20 $cmH_2O$, and the patient is ventilated at the new PEEP level in step 510. In step 512, the functional residual capacity is again determined and displayed with respect to PEEP in the same manner as in step 506 at point 514. Curve 516 is formed in graph 110 from points 508 and 514.

Figure 14:
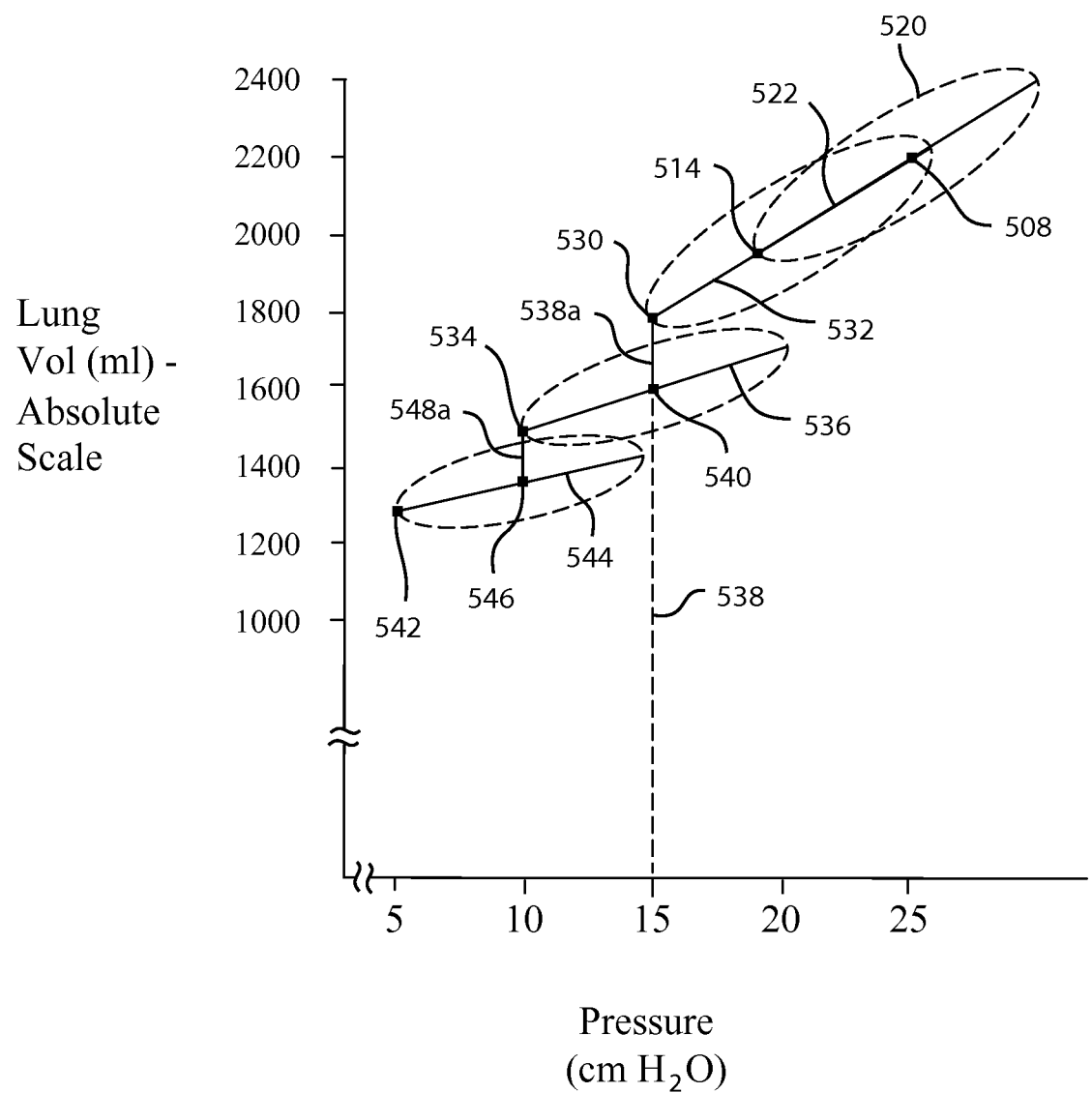
FIG. 14 is a graph showing the manner in which recruited/de-recruited volume is determined by the present invention.

A dynostatic curve is also obtained for the ventilation of the patient's lungs at the PEEP of 20 $cmH_2O$. FIG. 14 shows the spirometry data obtained at step 518 for the PEEP of 20 $cmH_2O$. For ease of explanation, the spirometry loop is shown simply as an ellipse 520 and dynostatic curve 522 shown as a straight line, it being understood that the spirometry loops and curves will actually resemble those shown in FIG. 10. However, the ordinate of the graph of FIG. 14 is scaled in absolute volume, not the relative volume of FIG. 10, so as to show functional residual capacity, as noted in steps 506 and 512.

The origin for dynostatic curve 522 will be the PEEP value of 20 $cmH_2O$ and the associated functional residual capacity value so that the origin corresponds to point 514 of FIG. 12 and FIG. 14. FIG. 14 can be seen as an enlargement of FIG. 12 showing the data used to generate the data of FIG. 12 and also showing dynostatic loops and curves. FIG. 14 shows a significant amount of data relating to the condition of the lungs of patient 12. The graph 110 of screen 102g6 of FIG. 12 shows the salient features of that data, thereby to assist and facilitate the selection of an optimal PEEP for patient 12 by the clinician.

Steps 510, 512 and 518 are then repeated for the next decremented PEEP of 15 $cmH_2O$. This produces a new point 530 of functional residual capacity and PEEP in curve 516 in FIGS. 12a and 12b and in FIG. 14. It also produces a new spirometry loop and dynostatic curve 532. Steps 510, 512, and 518 are again repeated for a PEEP of 10 $cmH_2O$ to produce point 534 and dynostatic curve 536 shown in FIG. 14.

Steps 524, 526 and 528 are used to determine the amount of recruited or de-recruited volume obtained in the lungs of patient 12. At PEEPs of 15 and 10 $cmH_2O$, some de-recruitment of lung volume is noted and steps 524, 526 and 528 of FIG. 13 are explained in conjunction with these PEEPs. In step 524 and using the dynostatic curve 536 for the reduced PEEP of 10 $cmH_2O$, the volume of the lungs at a pressure corresponding to that of the previous PEEP of 15 $cmH_2O$ is determined. Graphically, this may be accomplished by establishing vertical line 538 in of FIG. 14 at the previous PEEP of 15 $cmH_2O$ and noting the intersection of line 538 and dynostatic curve 536 at point 540.

The amount of volume on the ordinate scale represented by the line segment 538a between points 530 and 540 is also determined. In the present instance, this amounts to approximately 180 ml. In step 528, this value is placed in table 112 of screen 102g6 in association with the previous PEEP of 15 $cmH_2O$. In step 526, point 540 is placed in graph 110 of screen 102g5 as shown in FIGS. 12a and 12b.

FIG. 12b shows the completed Lung INview process, including the final measurement of functional residual capacity at a PEEP of 5 $cmH_2O$. This is carried out by repeating steps 510, 512, and 518, for a PEEP of 5 $cmH_2O$ to produce plot 542 of functional residual capacity and PEEP and dynostatic curve 544. Repeating steps 524, 526, and 528 produces point 546 and line segment 548a representing a volume of about 120 ml. The data is displayed in a manner corresponding to that described above in graph 110 and table 112 of screen 102g6. As the determination of the "difference" requires both functional residual capacity measurement taken at a previous PEEP and a dynostatic curve from subsequent PEEP and is referenced to the previous PEEP, no difference value will appear in the graph and table of screen 102g6 of FIG. 12b for the 5 $cmH_2O$ level of PEEP.

Reverting now to the situation with respect to the PEEPs of 25 and 20 $cmH_2O$, as noted above, at these higher PEEPs, there is little de-recruitment of lung volume as the alveolar sacs are continuously open during the respiratory cycle. This is expressed in FIG. 14 by the fact that dynostatic curve 522 for a PEEP of 20 $cmH_2O$ passes through point 508 formed using the functional residual capacity for a PEEP of 25 $cmH_2O$. Thus, no difference of the type represented by lines 538a and 548a will be seen when the PEEP is reduced from 25 $cmH_2O$ to 20 $cmH_2O$. This fact is shown as 0 difference in table 112 for a PEEP of 25 cmH$_2$O, since, as noted at step 528, the difference is tabulated to the previous PEEP.

An analogous situation exists for dynostatic curve 532 generated for the PEEP of 15 cmH$_2$O. That is, dynostatic curve 532 passes through point 514 formed using the functional residual capacity for 20 cmH$_2$O. Again, there is a zero difference as tabulated in table 112 for 20 cmH$_2$O. In graph 110 of FIGS. 12a and 12b, where the difference approximates zero, the differences determined in step 528 and the plot of the functional residual capacity at the previous PEEP are roughly the same and overlapping.

However, as the PEEP is further decremented, de-recruitment of lung volume begins to occur. For example, point 530 shows that for a PEEP of 15 cmH$_2$O, when the lung pressure is at that level, the lung volume is about 1800 ml. But when the PEEP is lowered to 10 cmH$_2$O, for a pressure in the lungs of 15 cmH$_2$O, the lung volume is only about 1620 ml, as evidenced by the plot of point 540. There has thus been a lung volume de-recruitment of approximately 180 ml when the PEEP was lowered from 15 cmH$_2$O to 10 cmH$_2$O, as evidenced by the length of line segment 538a.

An analogous situation exists when the PEEP is lowered from 10 cmH$_2$O to 5 cmH$_2$O as shown by line segment 548a. The de-recruitment of lung volume in that case is about 120 ml.

It will be appreciated, that a clinician may readily discern an optimal PEEP for patient 12 from the graphic and tabular data provided in screen 102g6 of FIG. 12b. Right after the recruitment maneuver of step 500, and for the higher PEEPs of 25 and 20 cmH$_2$O, the alveolar sacs will remain generally open during breathing due to the higher pressures. While this is advantageous from the standpoint of lung volume, the high pressure may be injurious to the patient. There is little reduction, or de-recruitment of lung volume as expiration proceeds to the end expiratory pressure, as shown in FIG. 12.

As PEEP is further reduced to 15 cmH$_2$O and then to 10 cmH$_2$O, a difference in volume will occur and curve 548 will separate below curve 516 in graph 110. The clinician will be able to note that at a PEEP of 10 cmH$_2$O, a portion of the lung volume that had been open at a PEEP of 15 cmH$_2$O will remain closed as pressure is increased from the PEEP of 10 cmH$_2$O to 15 cmH$_2$O during the course of inspiration while moving up the dynostatic curve. This difference, 180 ml in the example shown in FIGS. 12a and 12b and line segment 538a of FIG. 14, represents the "de-recruitment" of lung volume as the PEEP was reduced from 15 cmH$_2$O to 10 cmH$_2$O. Conversely, a volume would be "recruited" if the PEEP was increased from 10 cmH$_2$O to 15 cmH$_2$O.

Further lowering the PEEP to 5 cmH$_2$O results in an additional de-recruited loss of lung volume of 120 ml as shown by line segment 548a. As can be seen from the graph, the lung begins to lose volume or "derecruits" at PEEP settings below 15 cmH$_2$O and this suggests that 15 cmH$_2$O is a PEEP that is best suited or optimal for patient 12. In selecting an optimal PEEP, the clinician may set the PEEP at 15 cmH$_2$O so as to obtain some recruitment of lung volume over a PEEP of 10 cmH$_2$O. This may be preceded by a recruitment maneuver, such as at step 500, if desired. Or, the clinician may leave the PEEP at 10 cmH$_2$O since some recruitment is obtained at that level of PEEP.

As described above in connection with the determination of functional residual capacity, the determination of a suitable PEEP can be set to automatically occur in conjunction with certain procedures carried out by ventilator 10 or treatment procedures carried out on patient 12.

While the foregoing describes an example in which PEEP is decreased as the amount of recruitment or de-recruitment is determined, it will be appreciated that the technique may also be carried out using incremented, increasing values of PEEP.

Various alternatives and embodiments are contemplated as being within the scope of the following claims particularly pointing out and distinctly claiming the subject matter regarded as the invention.

What is claimed is:

1. A method for determining the extent to which a change in the functional residual capacity of a patient, occurring responsive to an alteration in a PEEP applied to the patient, results from recruitment/de-recruitment of lung volume, said method comprising the steps of:
   (a) providing breathing gases to the patient from a source of breathing gases during inspiration and allowing the removal of breathing gases from the patient during expiration;
   (b) applying a PEEP to the lungs of the patient at the end of expiration;
   (c) establishing an initial level of PEEP for the patient;
   (d) determining the functional residual capacity of the patient at the initial PEEP level;
   (e) altering the PEEP from the initial level to a higher or lower level;
   (f) determining the functional residual capacity of the patient at the altered PEEP level;
   (g) obtaining the relationship between lung gas pressures and breathing gas volumes during inspiration and expiration by the patient with the lower of the initial or altered PEEP levels applied to the patient; and
   (h) determining the difference in lung volume between the functional residual capacity for the higher of the initial or altered PEEP levels and the lung volume indicated by the lower PEEP level, pressure-volume relationship at a pressure corresponding to the higher PEEP level, the difference in lung volume comprising the lung volume recruited/de-recruited as a result of the alteration of the PEEP.

2. The method according to claim 1 wherein step (e) is further defined as altering the PEEP from a higher level to a lower level.

3. The method according to claim 1 wherein step (e) is further defined as altering the PEEP to a plurality of higher or lower levels, and the method is further defined as repeating steps (f) through (h).

4. The method according to claim 3 wherein step (e) is further defined as altering the PEEP from a higher level to a plurality of lower levels.

5. The method according to claim 3 further including the step of presenting, on a display, levels of applied PEEP and related lung volume differences.

6. The method according to claim 5 further defined as graphically presenting the PEEP levels, functional residual capacities of the patient, and lung volume differences.

7. The method according to claim 5 further defined as presenting the levels of PEEP, functional residual capacities of the patient, and lung volume differences in tabular form.

8. The method according to claim 3 further including the step of selecting the PEEP to be applied to the patient during ventilation using the determined functional residual capacities and lung volume differences.

9. The method according to claim 1 further including the step of presenting, on a display, a level of applied PEEP and related lung volume difference.

10. The method according to claim 1 wherein step (g) is further defined as expressing the lung gas pressure-breathing gas volume relationship as a spirometry, dynostatic curve.

11. The method according to claim 1 wherein steps (d) and (f) are further defined as determining the functional residual capacity of the patient by a gas wash in or wash out technique.

12. The method according to claim 1 further including an initial step of carrying out a lung volume recruitment maneuver to open the alveolar sacs in the patient's lungs.

13. A ventilator for ventilating a patient and for determining the extent to which a change in the functional residual capacity of the lungs of a patient, occurring responsive to an alteration in a PEEP applied to the patient by the ventilator, results from recruitment/de-recruitment of lung volume, said ventilator comprising:

at least one gas flow control valve in a flow path for breathing gases of the patient for establishing and altering the PEEP applied to the patient at a plurality of different levels;

a gas analyzer measuring a compositional characteristic of the breathing gases for the patient;

a sensor measuring a quantitative characteristic of the breathing gases of the patient;

central processing unit means coupled to said at least one gas flow control valve for operating same to establish a first level of PEEP applied to the patient and to alter the PEEP to a second level higher or lower than said first level, said central processing unit means being coupled to said gas analyzer and said sensor for determining the functional residual capacities of the patient at the differing levels of PEEP, for obtaining the relationship between lung gas pressures and breathing gas volumes during inspiration and expiration by the patient with the lower PEEP level applied to the patient, and for determining the difference in lung volume between the functional residual capacity for the higher PEEP level and the lung volume indicated by the lower PEEP level, pressure-volume relationship at a pressure corresponding to the higher PEEP level, the difference in lung volume comprising the lung volume recruited/de-recruited as a result of the alteration of the PEEP; and a display coupled to said central processing unit means and presenting the levels of PEEP applied to the patient and related recruited/de-recruited lung volumes.

14. The ventilator according to claim 13 wherein said central processing unit means operates said at least one gas flow control valve to alter the PEEP from a higher level to a lower level.

15. The ventilator according to claim 13 wherein said central processing unit means operates said at least one gas flow control valve to increment or decrement the PEEP to alter the PEEP applied to the patient.

16. The ventilator according to claim 13 wherein said central processing unit means obtains the lung gas pressure-breathing gas volume relationship as a spirometry, dynostatic curve.

17. The ventilator according to claim 13 wherein said central processing unit means determines the functional residual capacity of the patient from the wash in or wash out of an inert gas in the lungs of the patient.

18. The ventilator according to claim 13 wherein said display is further defined as graphically presenting the PEEP levels, functional residual capacities of the patient, and lung volume differences.

19. The ventilator according to claim 13 wherein said display is further defined as presenting the levels of PEEP, functional residual capacities of the patient, and lung volume differences in tabular form.

20. The ventilator according to claim 13 wherein said central processing unit means is further defined as operating said gas flow control valve to carry out a lung volume recruitment maneuver to open the alveolar sacs in the patient's lungs.

* * * * *